United States Patent [19]

Conrad et al.

[11] Patent Number: 5,380,716
[45] Date of Patent: Jan. 10, 1995

[54] SULFATED POLYSACCHARIDES AS INHIBITORS OF SMOOTH MUSCLE CELL PROLIFERATION

[75] Inventors: H. Edward Conrad; Peter Fugedi; Brian K. Brandley, all of Alameda; Lun H. Lam, Cupertino; Roger A. Laine, Alameda, all of Calif.

[73] Assignee: Glycomed, Inc., Alameda, Calif.

[21] Appl. No.: 996,894

[22] Filed: Dec. 28, 1992

Related U.S. Application Data

[63] Continuation-in-part of Ser. No. 686,540, Apr. 17, 1991, abandoned, which is a continuation-in-part of Ser. No. 400,661, Aug. 31, 1989, Pat. No. 5,032,679, which is a continuation-in-part of Ser. No. 285,546, Dec. 15, 1988, abandoned.

[51] Int. Cl.$^6$ .................. A61K 31/725; C08B 37/10
[52] U.S. Cl. .................................. 514/56; 514/54; 536/17.2; 536/17.5; 536/17.6; 536/18.7; 536/21
[58] Field of Search ............ 514/56, 54, 42; 536/21, 536/18.7, 17.2, 17.5, 17.6, 17.9, 22.1

[56] References Cited

U.S. PATENT DOCUMENTS

| | | | |
|---|---|---|---|
| 4,401,662 | 8/1983 | Lormeau et al. | 424/183 |
| 4,943,630 | 7/1990 | Jacquinet et al. | |
| 5,019,562 | 5/1991 | Folkman et al. | 514/58 |
| 5,032,679 | 7/1991 | Brandley et al. | 536/21 |

OTHER PUBLICATIONS

Benitz, William, "Inhibition by Heparin of Proliferation of Vascular Smooth Muscle Cells," in A. P. Fishman, "The Pulmonary Circulation: Normal and Abnormal", published 1988 by University of Pennsylvania Press (Philadelphia, Pa., USA), pp. 1–30.

Austin et al., "Intimal Proliferation of Smooth Muscle Cells as an Explanation for Recurrent Coronary Artery Stenosis After Percutaneous Transluminal Coronary Angioplasty," *J. Am. Coll. Cardiol.*, (1985), 6(2):369–375.

Guo et Conrad, "Analysis of Oligosaccharides from Heparin by Reversed-Phase Ion-Pairing High-Performance Liquid Chromatography," *Analy. Biochem.*, (1988), 168:54–62.

Clowes and Karnowsky, "Suppression by Heparin of Smooth Muscle Cell Proliferation in Injured Arteries," *Nature*, (1977), 265:625–626.

Marcum et al., "Heparan Sulfate Species and Blood Vessel Wall Function," *Biology of Proteoglycans*, (1987), Academic Press, pp. 301–343.

Castellot, Jr., et al., "Inhibition of Vascular Smooth Muscle Cell Growth by Endothelial Cell-derived Heparin," *J. Biol. Chem.*, (1982), 257:11256–11260.

Benitz et al., "Heparin Inhibits Proliferation of Fetal Vascular Smooth Muscle Cells in the Absence of Platelet-Derived Growth Factor," *J. Cell. Physiol.*, (1986), 127:1–7.

Orlidge and D'Amore, "Cell Specific Effects of Glycosaminoglycans on the Attachment and Proliferation of Vascular Wall Components," *Microvascular Res.*, (1986), 31:41–53.

Benitz, "The Pulmonary Circulation: Normal and Abnormal," Fishman, A. P., ed., University of Pennsylvania Press, (1988).

(List continued on next page.)

Primary Examiner—John W. Rollins
Assistant Examiner—Kathleen Kahler Fonda
Attorney, Agent, or Firm—Fish & Richardson

[57] ABSTRACT

Highly sulfated oligosaccharides in the form of hexasaccharide and octasaccharide compounds which have antiproliferative activity with respect to smooth muscle cells are useful in treatment of conditions characterized by unwanted smooth muscle cell proliferation such as a result of trauma or disease states such as asthma, congestive heart failure and hypertension. The oligosaccharides have increased ability to inhibit the proliferation of smooth muscle cells and decreased ability to act as an anticoagulant as compared with commercial heparin and/or unseparated fragments of heparin.

17 Claims, 10 Drawing Sheets

OTHER PUBLICATIONS

Castellot, Jr., et al., "Structural Determinants of the Capacity of Heparin to Inhibit the Proliferation of Vascular Smooth Muscle Cells," *J. Cell. Physiol.*, (1984), 120:315–320.

Castellot, Jr.; et al., "Structural Determinants of the Capacity of Heparin to Inhibit the Proliferation of Vascular Smooth Muscle Cells. II. Evidence for Pentasaccharide Sequence That Contains a 3-O-Sulfate Group" *J. Cell. Biol.*, (1986), 102:1979–1984.

Barzu et al., "Heparin-Derived Oligosaccharides: Affinity for Acidic Fibroblast Growth Factor and Effect on Its Growth-Promoting Activity for Human Endothelial Cells," *J. Cell. Physiol.*, (1989), 140:538–548.

Wright, Jr., et al., "Structural Determinants of Heparin's Growth Inhibitory Activity," *J. Biol. Chem.*, (1989), 264(3):1534–1542.

Casu, B., "Strucuture and Biological Activity of Heparin," *Adv. Carbohydrate Chem. & Biochem.*, (1985), 43:51–135.

Scott-Burden et al., "Artherosclerosis and Heparinoid-Matrix Interactions," *TIPS*, (1988), 9:95–97.

Pejler et al., "Monoclonal Antibodies Specific for Oligosaccharides Prepared by Partial Nitrous Acid Deamination of Heparin," *J. Biol. Chem.*, (1988), 263(11):5197–5201.

Conrad, H., "Structure of Heparan Sulfate and Dermatan Sulfate," *Heparin and Related Polysaccharides*, (1989), 556:18–28.

International (PCT) Search Report, International Application No. PCT/US89/05559.

FIG. 6A
n=2

| | A | B | A' | B' | C' | D |
|---|---|---|---|---|---|---|
| 1 | X | X | | | X | X |
| 2 | X | X | | | X | |
| 3 | X | X | | | | |
| 4 | | X | | | X | X |
| 5 | | X | | | X | |
| 6 | X | X | | | | X |
| 7 | | | | | X | X |
| 8 | X | | | | X | X |
| 9 | X | | | | X | |
| 10 | X | | | | | X |
| 11 | | X | | | | X |
| 12 | X | X | X | | X | X |
| 13 | X | X | X | | X | |
| 14 | X | X | X | | | |
| 15 | | X | X | | X | X |
| 16 | | X | X | | X | |
| 17 | X | X | X | | | X |
| 18 | | | X | | X | X |
| 19 | X | | X | | X | X |
| 20 | X | | X | | X | |
| 21 | X | | X | | | X |
| 22 | | X | X | | | X |

FIG. 6B
n=2

| | A | B | A' | B' | C' | D |
|---|---|---|---|---|---|---|
| 23 | X | X | | X | X | X |
| 24 | X | X | | X | X | |
| 25 | X | X | | X | | |
| 26 | | X | | X | X | X |
| 27 | | X | | X | X | |
| 28 | X | X | | X | | X |
| 29 | | | | X | X | X |
| 30 | X | | | X | X | X |
| 31 | X | | | X | X | |
| 32 | X | | | X | | X |
| 33 | | X | | X | | X |
| 34 | X | X | X | X | X | X |
| 35 | X | X | X | X | X | |
| 36 | X | X | X | X | | |
| 37 | | X | X | X | X | X |
| 38 | | X | X | X | X | |
| 39 | X | X | X | X | | X |
| 40 | | | X | X | X | X |
| 41 | X | | X | X | X | X |
| 42 | X | | X | X | X | |
| 43 | X | | X | X | | X |
| 44 | | X | X | X | | X |

FIG. 6C
n=2

| | A | B | A' | B' | C' | D |
|---|---|---|---|---|---|---|
| 45 | | | X | X | | |
| 46 | X | | X | X | | |
| 47 | | X | X | X | | |
| 48 | | | X | X | X | |
| 49 | | | X | X | | X |
| 50 | X | | X | | | |
| 51 | | X | X | | | |
| 52 | | | X | | X | |
| 53 | | | X | | | X |
| 54 | X | | | X | | |
| 55 | | X | | X | | |
| 56 | | | | X | X | |
| 57 | | | | X | | X |
| 58 | | | | | | |
| 59 | | | | | | |
| 60 | | | | | | |
| 61 | | | | | | |
| 62 | | | | | | |
| 63 | | | | | | |
| 64 | | | | | | |
| 65 | | | | | | |
| 66 | | | | | | |

SULFATED POLYSACCHARIDES AS INHIBITORS OF SMOOTH MUSCLE CELL PROLIFERATION

CROSS-REFERENCES

This application is a continuation-in-part of U.S. Ser. No. 07/686,540 filed Apr. 17, 1991 (now abandoned), which application is a continuation-in-part of U.S. Ser. No. 07/400,661 filed Aug. 31, 1989 (U.S. Pat. No. 5,032,679 issued Jul. 16, 1991), which application is a continuation-in-part of U.S. Ser. No. 07/285,546 filed Dec. 15, 1988 (abandoned), all of which applications are incorporated herein by reference and to which applications is claimed priority under 35 USC Section 120.

TECHNICAL FIELD

The invention relates to the use of carbohydrate preparations as therapeutic and diagnostic compositions. In particular, the invention relates to polysaccharides having six or more saccharide units and compositions containing such polysaccharides which are useful in treating diseases and conditions characterized by excessive smooth muscle cell proliferation.

ABBREVIATIONS

In the representations of oligomers produced synthetically and those derived from heparin, the following abbreviations are used: D-glucuronic acid=GlcA; L-iduronic acid=IdoA; D-glucosamine=GlcNH$_2$; N-acetyl-D-glucosamine=GlcNAc; D-glucosamine N-sulfate=GlcNS; 2,5-anhydromannose=Man(2,5); 2,5-anhydromannitol=ManH(2,5); D-xylose=Xyl; glycosaminoglycan=GAG.

The location of the O-linked sulfate residues is indicated by "S" and the number of the position of sulfation where the sulfate residue is linked to oxygen on the sugar residue. In these designations, also, the alpha and beta anomeric linkages are as those conventionally found in heparin and the indicated D or L configurations as conventionally found pertains. The locations of the sulfates are shown below the abbreviation for the sugar to which they apply, thus, for example,

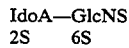

refer to L-iduronic acid and D-glucosamine N-sulfate with sulfates connected respectively at the 2 and 6 positions of the sugar residues.

BACKGROUND ART

Proliferation of smooth muscle cells in blood vessel walls occurs in response to vascular injury, and in association with certain disease states (Austin, G. E., et al., *J Am Coll Cardiol* (1985) 6:369–375). The proliferation of these cells can have negative effects due to the production of excess proteins or other matrix molecules, which, along with the cells themselves, form pathologic lesions of, for example, atherosclerosis, renal hypertension, pulmonary hypertension, vasculitis, and post-surgical vascular retinosis. These results are distinguished from the acute response to trauma characterized by blood clotting.

Glycosaminoglycans (GAG) are copolymers of alternating hexosamine and aldouronic acid residues which are found in sulfated forms and are synthesized as proteoglycans. They have collectively been called mucopolysaccharides, and those in heparin are more precisely called glycosaminoglycuronans.

To place the compositions discussed below in context, it may be noted that heparin and heparan sulfate are members of the GAG family which are classified by the nature of the hexosamine/aldouronic acid repeating units. For example, in chondroitin sulfates, the aldouronic acid is primarily D-glucuronic acid, and the hexosamine is N-acetylated 2-amino-2-deoxy-D-galactose, more commonly known as N-acetyl galactosamine and abbreviated as GalNAc.

In dermatan sulfate (chondroitin sulfate B) the aldouronic acid is mostly L-iduronic acid and the hexosamine is GalNAc. In keratan sulfate, the aldouronic acid is replaced by D-galactose, and the hexosamine is mostly N-acetylated 2-amino-2-deoxy-D-glucose, more commonly known as N-acetyl glucosamine and abbreviated as GlcNAc.

In the compositions of interest herein, heparan sulfate and heparin, the hexosamine is mostly N-acetylated or N-sulfated glucosamine (GlcN), and the aldouronic acid is mostly L-iduronic in heparin and mostly D-glucuronic acid in heparan sulfate. Heparan sulfate is commonly considered to have a higher proportion of glucuronic acid than heparin.

Problems of heterogeneity in preparations of heparan sulfate or heparin isolated from tissues make sharp distinctions difficult, since these oligosaccharides are related by the biosynthesis pathway, as explained below. Conventional heparin (used as an anticoagulant) has a molecular weight of 5–25 kDa and is extracted as a mixture of various chain lengths by conventional procedures. These procedures involve autolysis and extraction of suitable tissues, such as beef or porcine lung, intestine, or liver, and removal of other GAGs as well as nonpolysaccharide components.

The molecular weight of the chains in the extract is significantly lower than the 60–100 kd known to exist in the polysaccharide chains of the heparin proteoglycan synthesized in the tissue. The GAG moiety is synthesized bound to a peptide matrix at a serine residue through a tetrasaccharide linkage region of the sequence D-GlcA-D-Gal-D-Gal-D-Xyl→protein, which is then elongated at the D-GlcA residue with alternate additions of GlcNAc and GlcA.

The polysaccharide sidechains are modified by a series of enzymes which sequentially deacetylate the N-acetyl glucosamine and replace the acetyl group with sulfate, epimerize the hydroxyl at C5 of the D-glucuronic acid residue (to convert it to L-iduronic acid), sulfate the 0–2 of the resulting L-iduronic acid and the 0–6 of the glucosamine residue. Some of the chains are further sulfated at the 0–3 of the glucosamine residue, either at the heparan or heparin stage. This latter sulfation generates the active sequence required for anti-thrombin III binding and thus anticoagulation activity. Other chemically possible sulfation sites are on the 0–2 of D-glucuronic acid.

Due to their obvious chemical similarity, isolated "heparin" may contain considerable amounts of what might otherwise be classified as heparan sulfate.

There is an extensive body of art concerning depolymerization of heparin/heparan sulfate chains and separation of products by size. Particularly relevant is the report of Guo, Y. et al., *Anal Biochem* (1988) 168:54–62 which discloses the results of structure determination after the 2,5-anhydromannose at the reducing terminus is reduced to the corresponding 2,5-anhydromannitol.

The involvement of heparin or heparan sulfate or degradation products thereof in smooth muscle proliferation has been recognized for some time. Heparin and heparan sulfate can slow or arrest the vascular smooth muscle cell proliferation associated with injury described hereinabove (Clowes, A. W., et al., *Nature* (1977) 265:625–626). The effect of heparan sulfate and heparin on smooth muscle cell proliferation is also described by Marcum, J. A., et al. in *Biology of Proteoglycan,* Academic Press (1987) pp. 301–343. The inhibition of vascular smooth muscle cell growth by heparin was further described by Casteliot, J. J., Jr., et al., *J Biol Chem* (1982) 257:11256–11260 and the effect of heparin on vascular smooth muscle cell growth in fetal tissue was described by Benitz, W. E., et al., *J Cell Physiol* (1986) 127:1–7. The effect of heparin as an inhibitor of both pericyte and smooth muscle cell proliferation was shown by Orlidge, A., et al., *Microvascular Research* (1986) 31:41–53, and these authors further showed that chondroitin sulfate and dermatan sulfate do not have this effect. A review of the effects of heparin and heparan sulfate on the proliferation of smooth muscle cells is by Benitz, W. E. in "The Pulmonary Circulation: Normal and Abnormal", Fishman, A. P., ed., University of Pennsylvania Press (1988).

It is not clear by what mechanism these glycosaminoglycans operate, or to what extent they interact with other growth factors such as epithelial and fibroblast growth factors. It has been proposed that a 3-O sulfate on glucosamine in an oligosaccharide of at least 5 sugars is important in this process and that both O-and N-sulfation is important (Casteliot, J. J., et al., *J Cell Physiol* (1984) 120:315–320; Casteliot, J. J., et al., *J Cell Biol* (1986) 102:1979–1984). Hexasaccharides-decasaccharides obtained from partial nitrous acid digestion of heparin bind to acidic fibroblast growth factor and aid its mitogenic activity in fibroblasts, but inhibit the proliferation of endothelial cells under some conditions (Barzu, T., et al., *J Cell Physiol* (1989) 140:538–548). The effective hexasaccharide was stated to have the structure:

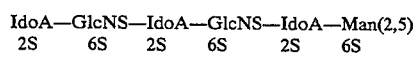

Others have indicated that the presence of 2-O-sulfate glucuronic acid is not necessary for antiproliferative activity (Wright, Jr., T. C., et al., *J Biol Chem* (1989) 264:1534–1542). In this article, size separated fragments of defined length prepared by nitrous acid cleavage and gel filtration were further separated according to charge for some assays. Partially digested heparin separated only according to size was tested with respect to stimulation of the growth of smooth muscle cells and epithelial cells. Similar results were found in both cases, although the results were not identical. Tetrasaccharides of the type tested were shown to have very low antiproliferative activity; hexasaccharides, octasaccharides, and decasaccharides were shown to be active to approximately the same level on a weight/volume concentration basis. Also tested was a synthetic pentapeptide which represents a unique sequence of the heparin required for the binding of heparin to antithrombin III; this pentapeptide was active in inhibiting proliferation for smooth muscle but not epithelial cells. The size-separated fractions were then treated chemically to produce "O-oversulfation" and this treatment enhanced the inhibitory activity; indeed, oversulfation of the tetrasaccharide fragment preparation yielded a tetrasaccharide fraction which was active in inhibiting proliferation. The converse process, comprising desulfation and reacetylation of the amino groups of glucosamine results in a reduction in antiproliferative activity. These fragments could, however, be made more active by subsequent oversulfation.

Also capable of reducing the activity of the heparin fragments was reduction of the carboxyl groups so as to reduce the total negative charge. O-oversulfation partially restores this activity. These results with N-desulfated, N-acetylated fragments which are lacking in antiproliferative activity is distinguishable from previous results wherein similarly treated heparin retains the capacity to prevent cell division because of the size dependency of the antiproliferative activity-larger fragments being more powerful in general than smaller ones.

When the size separated fraction was further fractionated according to charge, it was found that the most highly charged fractions showed the greatest activity. Furthermore, it was shown that although the synthetic pentasaccharide identified as the antithrombin III binding site is capable of inhibiting proliferation in smooth muscle cells, any treatment of heparin which would destroy the sequence corresponding to this pentapeptide (i.e., periodate treatment) does not destroy antiproliferative activity.

Methods of synthesizing oligosaccharides are disclosed in U.S. Pat. No. 4,943,630 issued Jul. 14, 1990 which is incorporated herein by reference to disclose such methods.

The present inventors have now found that an enhanced antiproliferative activity with respect to smooth muscle cells is associated with an oligosaccharide portion of the heparin or heparan sulfate GAGs which is highly sulfated and contains 6 or 8 saccharide units and have provided synthesis mechanisms for making polysaccharides containing 6 or more sugar residues, which oligosaccharides have enhanced antiproliferative activity with respect to smooth muscle cells.

DISCLOSURE OF THE INVENTION

The invention provides a low molecular weight glycosaminoglycan (GAG) composition which has superior specific antiproliferative activity with regard to smooth muscle cells. The existence of this activity in a low molecular weight GAG provides the opportunity for effective pharmaceutical compositions which can be prepared by synthesis or by isolation of the composition from natural sources.

Accordingly, in one aspect, the invention is directed to a process to prepare a sulfated polysaccharide having antiproliferative activity. The polysaccharides of the invention may be produced synthetically using a sequence of chemical reactions as disclosed herein or obtained by digesting heparin and carrying out separation procedures based on size and charge as disclosed herein.

In order to produce the polysaccharide compounds of the invention synthetically it is first necessary to synthesize an iduronic acid synthon. Next, a glucosamine synthon is produced. The iduronic acid synthon and glucosamine synthon are reacted to produce a disaccharide synthon. The disaccharide units can be reacted to form oligosaccharides containing 4, 6, 8 or any multiple thereof of monosaccharide units and/or can be reacted with either an iduronic or glucosamine reaction synthon to provide oligosaccharides containing any odd number of saccharide units.

In order to obtain the oligosaccharide compounds by digestion, the heparin is obtained from a natural source and subjected to digestion with nitrous acid under conditions which favor the formation of an oligosaccharide mixture containing large amounts of hexa- and octasaccharides. Following the digestion, the mixture is separated according to size and those factions corresponding to hexa- and octasaccharides are combined and recovered. The recovered portions are then separated according to charge in order to obtain the more highly charged fractions. These fractions will contain oligosaccharides which are highly sulfated. Polysaccharides sulfated at the 0–3 position of the GlcN (associated with anticlotting activity) are not encompassed by the present invention.

The invention is also directed to pharmaceutical compositions comprised of the oligosaccharides of the invention either alone or in combination with excipients, i.e., pharmaceutically acceptable materials with no pharmacological effect. Such compositions may be administered to a patient in order to regulate smooth muscle cell proliferation.

A primary object of the present invention is to provide synthetically produced oligosaccharides containing 6 or more monosaccharide units, which are highly sulfated at particular positions other than 0–3 positions of the GlcNs and which effect smooth muscle cell proliferation.

Another important object of the present invention is to provide a method of obtaining hexa- and octasaccharide units from natural heparin and heparan sulfate which hexa- and octasaccharide units are effective in regulating smooth muscle cell proliferation and which do not process any significant degree of anticlotting activity.

An advantage of the present invention is that the oligosaccharide units can be formulated into pharmaceutical compositions which can be administered to aid in the regulation of smooth muscle cell proliferation.

A feature of the present invention is that the oligosaccharide units include monosaccharide residues which are sulfated at particular positions (other than the 0–3 position) which effected the ability of the oligosaccharide to regulate smooth muscle cell proliferation.

These and other objects, advantages and features of the present invention will become apparent to those persons skilled in the art upon reading the details of the structure, synthesis and usage as more fully set forth below, reference being made to the accompanying figures and general structural formulas forming a part herein wherein like symbols refer to like molecular moieties throughout.

BRIEF DESCRIPTION OF THE DRAWINGS

FIGS. 6A, 6B and 6C are charts showing possible sulfated positions for fifty-seven octasaccharides of the invention.

DETAILED DESCRIPTION OF PREFERRED EMBODIMENTS

Figure 1A:
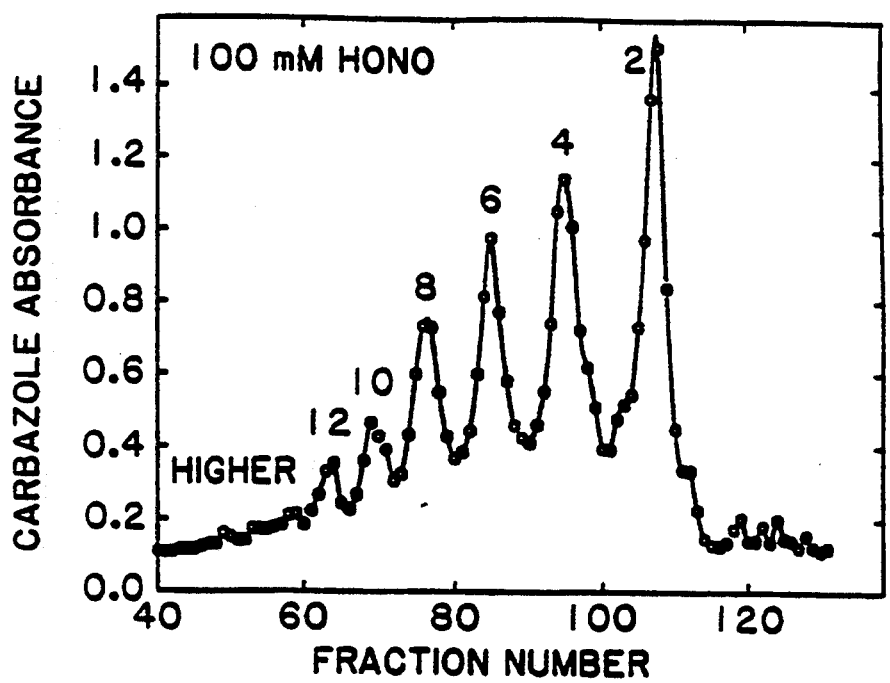
FIGS. 1A and 1B show the elution profiles from gel filtration chromatography of reaction mixtures produced using varying amounts of nitrous acid.
Figure 1B:
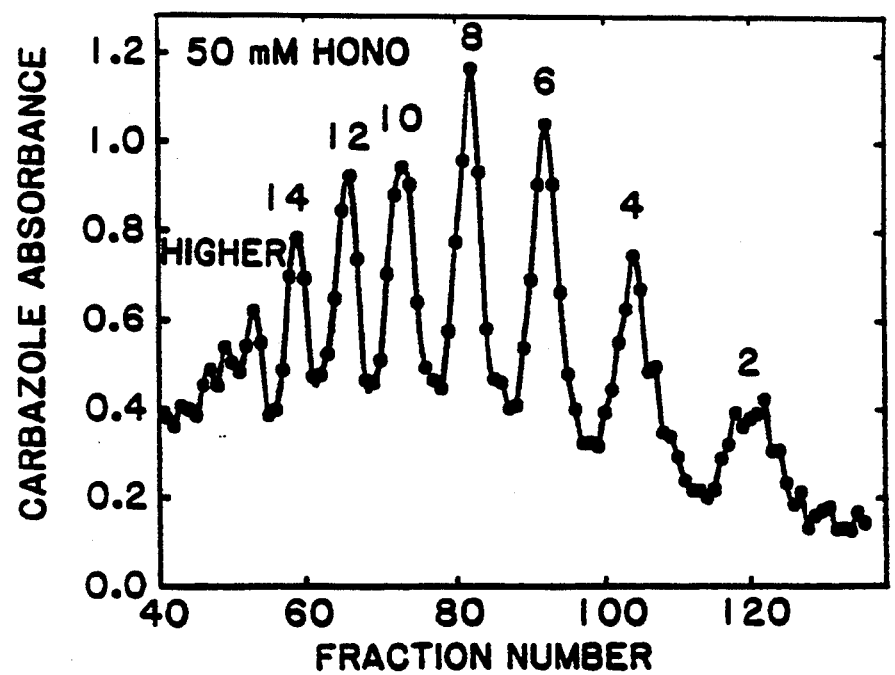

Before the present oligosaccharides and processes for making and formulating such are described, it is to be understood that this invention is not limited to the particular oligosaccharides, formulations or processes described as such compounds, compositions and methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the content clearly dictates otherwise. Thus, for example, reference to "an oligosaccharide" includes mixtures of oligosaccharides and, reference to "an octasaccharide" includes reference to mixtures of octasaccharides of the type described herein and reference to "the process step" or "the process" includes reference to various steps and processes of the type described herein which will be known to those skilled in the art or which will become apparent to those skilled in the art upon reading this disclosure and so forth.

Definitions

By "heparin/heparan sulfate" or "heparin" is meant a preparation obtained from tissues in a manner conventional for the preparation of heparin as an anticoagulant or otherwise synthesized and corresponding to that obtained from tissue. See Conrad, H. E., Heparin and Related Polysaccharides, Vol. 56, p. 18 of Annals of N.Y., Academy of Sc., Jun. 7, 1989, incorporated herein by reference. This preparation may include residues of D-glucuronic acid (GlcA), as characteristic of heparan sulfate as well as iduronic acid (IdoA) as characteristic of heparin. However, both GlcA and IdoA are present in both, they are present in different proportional amounts. The (IdoA)/GlcA ratio increases as heparan sulfate becomes more heparin-like. As described in the Background section above, the conversion of D-glucuronic acid to L-iduronic acid is a result of epimerization at the 5 carbon of GlcA residues in a heparan-type intermediate. This sequence of steps involved in such epimerization and conversion is understood in the art. To the extent that full conversion has not been made, heparan sulfate characteristics remain in the preparation. Because the precise nature of the polymeric chains in the preparations of heparin is not generally determined, and varies from preparation to preparation, the term "heparin/heparan sulfate" or "heparin" is intended to cover the range of mixtures encountered. Perhaps the main feature which distinguishes heparan sulfate from heparin is that the latter has anticoagulant activity.

The "heparin/heparan sulfate" preparation can be obtained from a variety of mammalian tissues, including, if desired, human tissue. Generally, porcine or bovine sources are used, and vascularized tissues are preferred. A preferred source of heparin/heparan sulfate starting material is porcine intestinal mucosa, and preparations labeled "heparin" prepared from this tissue source are commercially available. In general, the heparin/heparan sulfate starting material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin starting material are found, for example, in Charles, A. F., et al., *Biochem J* (1936) 30:1927–1933, and modifications of this basic procedure are also known, such as those disclosed by Coyne, E., in *Chemistry and Biology of Heparin*, Elsevier Publishers, North Holland, New York, Lunblad, R. L., et al., eds. (1981).

Synthetic Oligosaccharides

The synthetic oligosaccharides of the present invention include at least 6 saccharide residue units and have the following general structural formula:

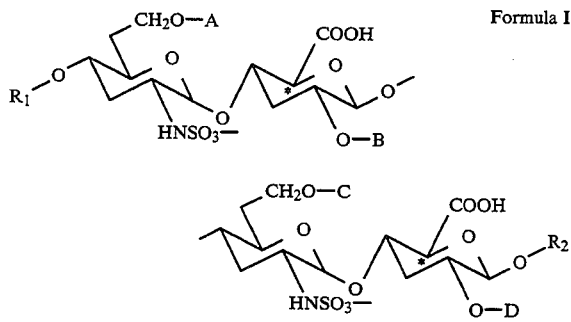

Formula I (The hydroxyl groups on the 3-position of the sugars have been omitted for greater clarity) and the * adjacent the carbon substituted with COOH indicates (here and throughout the application) undetermined stereochemistry which may be any possible stereochemistry for the molecule; wherein each of the variables A, B, C and D are independently hydrogen or SO$_3$R with the proviso that at least 2 of the variables are SO$_3$R and each R is independently H$^+$, Na$^+$, or other suitable cation; and wherein R$_1$ and R$_2$ are each independently hydrogen, or one or more repeating units having the following structure:

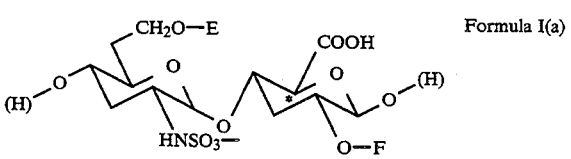

Formula I(a)

wherein when the unit of structural Formula I(a) is connected at one end the hydrogen is not present and the hydrogen at the end not connected is present and further wherein each of the variables E and F is independently hydrogen or SO$_3$R.

Some preferred embodiments of the present invention include compounds of structural Formula I wherein each of A, B, C and D are —SO$^-_3$ and either R$_1$ or R$_2$ is the unit of structural Formula I(a). Another preferred embodiment includes compounds of structural Formula I wherein each of A, B, C and D is —SO$^-_3$ and both R$_1$ and R$_2$ are the unit of structural Formula I(a) and wherein each E and F of the unit I(a) is —SO$^-_3$.

Polysaccharides Derived from Heparin and/or Heparan Sulfate

Preferably, the heparin/heparan sulfate preparation used as a starting material is first purified by extraction with a solvent in which the heparin is insoluble, such as ethanol or acetone. The purified starting material is then depolymerized.

Depolymerization in general can use various reagents, such as nitrous acid, heparinase or periodate. The antiproliferative compositions of the invention are obtainable when partial nitrous acid digestion is conducted under conditions which maximize formation of hexasaccharide and octasaccharide fragments.

In typical procedures, the nitrous acid is prepared in situ by acidification of a solution of sodium nitrite at a concentration of 50 mM, and the reagent is used to treat the heparin at a concentration of about 60–180 mg/ml, at a pH of about 1.0 to about 2.0, preferably about 1.5. The reaction is conducted at room temperature and can be neutralized by addition of a suitable reagent at the desired stage of digestion. Other depolymerization methods can be used as long as they produce active components, i.e., components which (1) are predominantly hexa- and octasaccharides; (2) are heavily sulfated; (3) have substantial antiproliferation activity with respect to smooth muscle cells; and (4) have insignificant or no anticlotting activity.

Isolated fragments can then be tested for their ability to inhibit smooth muscle cell proliferation. Fragments with high activity with respect to inhibiting the proliferation of smooth muscle cells and low activity with respect to their ability to inhibit blood coagulation (relative to commercial heparin) are preferred.

The depolymerization results in a mixture of fragments that is then separated on the basis of size. A variety of size separation techniques are available, including gel permeation, density gradient centrifugation; especially preferred is gel filtration chromatography using a Sephadex or polyacrylamide gel system with a fractionation range of about 100–3500 daltons. A particularly preferred gel permeation resin is Biogel P10, and upon separation using this method, fragments which are disaccharides, tetrasaccharides, hexasaccharides, octasaccharides, and oligosaccharides of higher molecular weights are effectively separated.

The fractions containing predominantly hexa- and octasaccharide units show enhanced activity in inhibiting the proliferation of smooth muscle cells. Verification of this property can be obtained using standard assays, such as those described in Castellot, J. J. Jr., et al., *J Cell Biol* (1986) 102:1979–1984. Other assay methods, such as those of Benitz, W. E., et al., *J Cell Physiol* (1986) 127:1–7 can also be used.

The hexasaccharide fragments thus obtained are of the formula:

Formula II

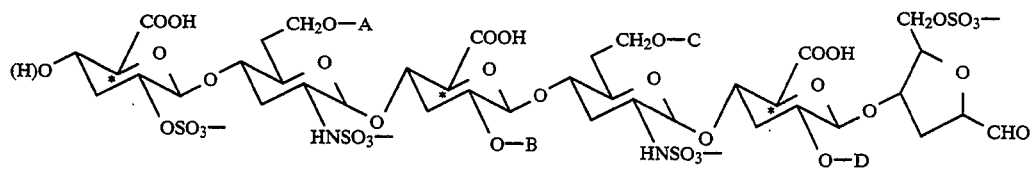

wherein each of the variables A, B, C and D is independently H or SO₃R and each R is independently H or a cation, with the proviso that at least two of the variables A, B, C or D is —SO₃R. It is pointed out that hydroxyl groups on 3-positions of the sugars have been omitted for greater clarity and the * adjacent the COOH indicates undetermined stereochemistry.

In the compounds of formula (II) the sugar at the reducing terminus is deaminated to form the 2,5-anhydromannose shown. When this compound is further reduced, the CHO shown becomes —CH₂OH; however, this reduction does not occur in the depolymerization reaction per se. This reduced form is a compound of the present invention as shown below in formula (IIa).

indicates a —SO₃R is present at the indicated A, B, C or D position.

TABLE 1

|     | A | B | C | D | = SO₃ |
| --- | - | - | - | - | ----- |
| 1.  | X | X | X | X |       |
| 2.  | X | X | X |   |       |
| 3.  |   | X | X | X |       |
| 4.  | X |   | X | X |       |
| 5.  | X | X |   | X |       |
| 6.  | X | X |   |   |       |
| 7.  | X |   | X |   |       |
| 8.  | X |   |   | X |       |
| 9.  |   | X | X |   |       |
| 10. |   | X |   | X |       |
| 11. |   |   | X | X |       |

Formula II(a)

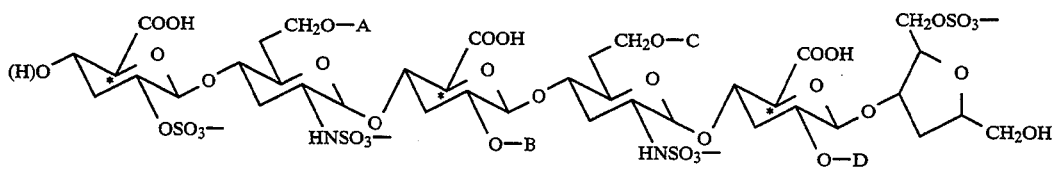

In the —SO₃R, the cations represented by R can either be inorganic cations such as sodium, potassium, calcium, or ammonium ion or can be organic cations such as those obtained from quaternary amines; these salts are formed by simple neutralization.

Based on the above formula (II) it can be seen that there are eleven different possible configurations with respect to the positions of —SO₃R moieties when 2 or more are present. These configurations are schematically shown in the following table wherein an "X"

In that each "R" can be any cation, the above eleven possible structures represent a significantly larger number of compounds, i.e., the acid and salt forms.

The basic structure of the eleven possible configurations shown by formula (1) and the above table are put forth below. Regarding the structures II(1)–II(11) it is pointed out that hydroxyl groups on the 3-position of the sugars have been omitted for greater clarity.

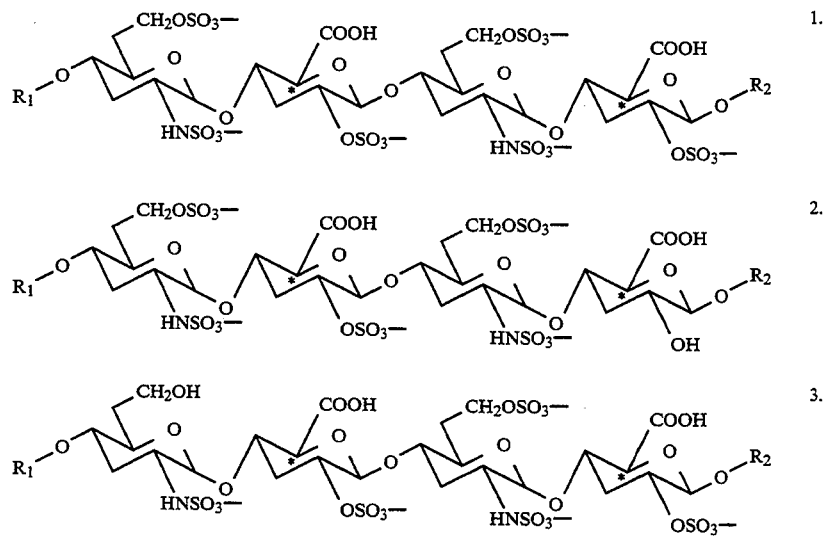

-continued

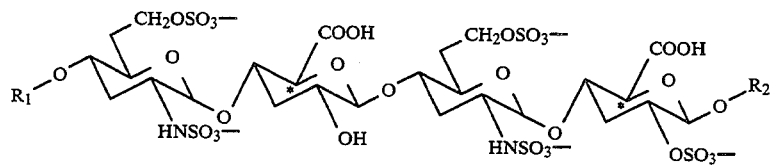
4.

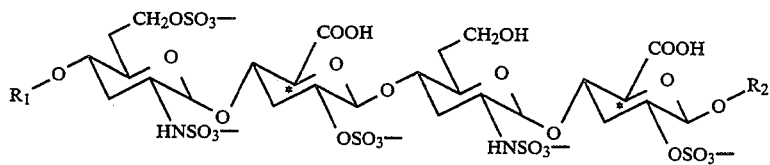
5.

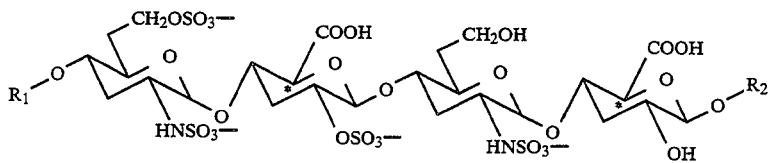
6.

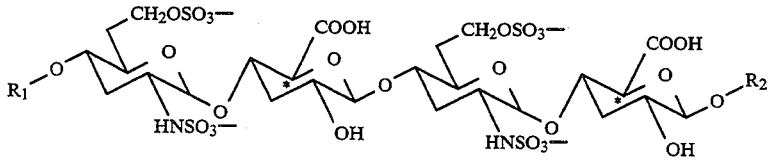
7.

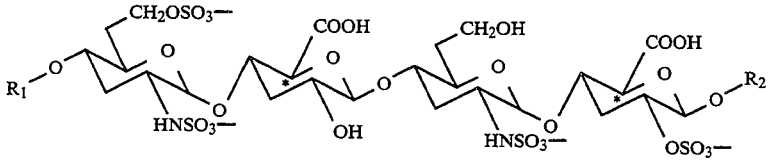
8.

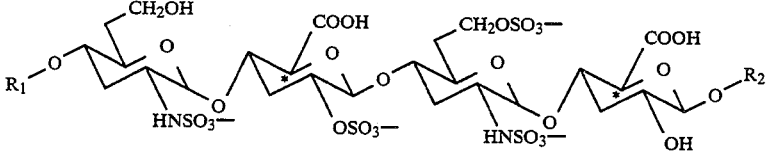
9.

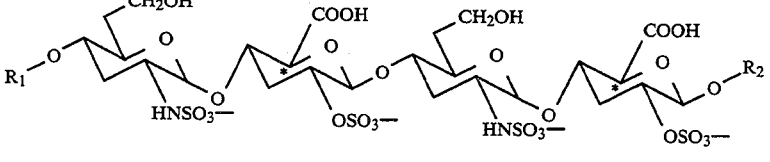
10.

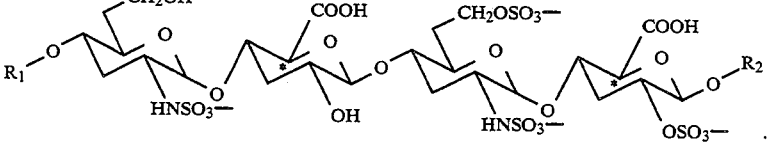
11.

Representative compounds of the invention, wherein R is as above defined are set forth as follows. In these representations, the following abbreviations are used: L-iduronic acid=IdoA; D-glucosamine=GlcNH$_2$; N-acetyl-D-glucosamine=GlcNAc; D-glucosamine N-sulfate=GlcNS; 2,5-anhydromannose=Man(2,5); 2,5-anhydromannitol=ManH(2,5). The location of the O-linked sulfate residues is indicated by "S" and the number of the position of sulfation where the SO$_3$R residue is linked to oxygen. In the designations below, the alpha and beta anomeric linkages are as those shown in formula 1 above and the indicated D or L configurations as set forth above pertains. The locations of the sulfates are shown below the abbreviation for the sugar to which they apply.

The hexasaccharide and octasaccharide fragments obtained by digesting heparin and following the above-described procedures are of the formula:

Formula III

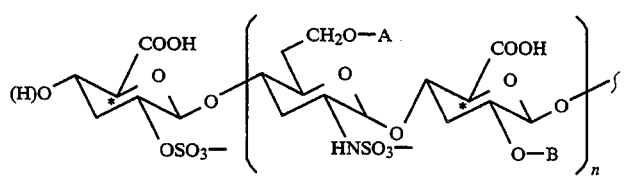

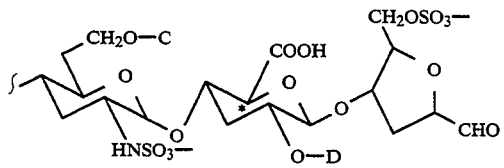

wherein n is 1 or 2, each of the variables A, B, C and D is independently H or SO₃R, wherein each R is independently H or a cation, with the proviso that at least two of said A, B, C and D are SO₃R. As in the Formulas I and II above, the hydroxyl groups in the 3 position of the sugars have been omitted for greater clarity and the asterisk next to the position of the carboxyl group indicates that the stereochemistry thereof is undetermined.

In the compounds of formula (III) the sugar at the reducing terminus is deaminated to form the 2,5-anhydromannose shown. When this sugar is further reduced, the CHO shown becomes —CH₂OH; however, the reduction does not occur in the depolymerization reaction per se. The reduced compound is part of the present invention and is shown below as formula (IIIa) wherein each of the variables is defined as in formula III above.

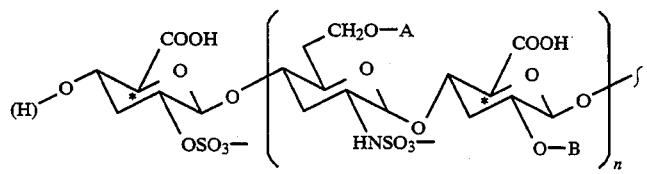

Formula III(a)

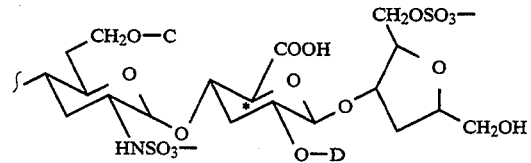

The cations represented by R can either be inorganic cations such as sodium, potassium, calcium, or ammonium ion or can be organic cations such as those obtained from quaternary amines and these salts are formed by simple neutralization. As above, the hydroxyls at the 3 positions are not shown in the structure, but are understood to be present, and the asterisk adjacent the position of the carboxyl groups indicates that the stereochemistry at these positions is undetermined.

Based on the above formula (III) it can be seen that there are fifty-seven different possible configurations with respect to the position of the —SO₃R moieties when 2 or more are present. These configurations are schematically shown in FIGS. 6A, 6B and 6C wherein an "X" indicates a —SO₃R is present at the indicated A, B, A', B', C or D position wherein A' and B' represent the embodiments of A and B in the parenthesized disaccharide unit proximal to the dehydromannose or dehydromannitol residue.

In that each "R" can be H or a cation, the fifty-seven possible structures represent a significantly larger number of compounds, i.e., the acid and salt forms.

The basic structural formulae of the fifty-seven configurations are not put forth herein. However, these formulae can be deduced from formula III and FIGS. 6A, 6B and 6C by referring to the formulae II(1)-II(11) above.

Preferred compounds of the invention are the hexasaccharides. However, the preferred octasaccharides include octasaccharides having antiproliferative activity with smooth muscle cells which have the formula

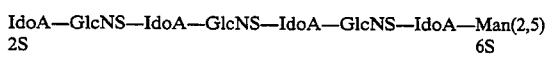

wherein at least two of the six sugars in the middle —GlcNS—IdoA—GlcNS—IdoA—GlcNS—IdoA— group include a sulfate; or a physiologically acceptable salt thereof.

Especially preferred among these are octasaccharides wherein at least two IdoA—GlcNY units are

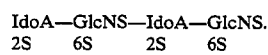

Thus, preferred octasaccharides of the invention include any of the following octasaccharides, their pharmaceutically acceptable salts and mixtures of two or more of such octasaccharides and their salts

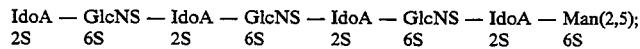

-continued

| | | | | | | | |
|---|---|---|---|---|---|---|---|
| IdoA 2S | — GlcNS 6S | — IdoA 2S | — GlcNS 6S | — IdoA 2S | — GlcNS 6S | — IdoA | — Man(2,5); 6S |
| IdoA 2S | — GlcNS 6S | — IdoA 2S | — GlcNS 6S | — IdoA 2S | — GlcNS | — IdoA 2S | — Man(2,5); 6S |
| IdoA 2S | — GlcNS 6S | — IdoA 2S | — GlcNS 6S | — IdoA | — GlcNS 6S | — IdoA 2S | — Man(2,5); 6S |
| IdoA 2S | — GlcNS 6S | — IdoA 2S | — GlcNS | — IdoA 2S | — GlcNS 6S | — IdoA 2S | — Man(2,5); 6S |
| IdoA 2S | — GlcNS 6S | — IdoA | — GlcNS 6S | — IdoA 2S | — GlcNS 6S | — IdoA 2S | — Man(2,5); and 6S |
| IdoA 2S | — GlcNS 2S | — IdoA 6S | — GlcNS 2S | — IdoA 6S | — GlcNS 2S | — IdoA 6S | — Man(2,5). |

Statement of Utility

The oligosaccharide compositions of the invention are useful in therapeutic applications for treatment of conditions or diseases which are characterized by excessive and destructive smooth muscle cell proliferation. These conditions frequently occur where the subject has been exposed to trauma, such as in the case of surgical patients. The trauma caused by wounds or surgery results in vascular damage and secondary smooth muscle cell proliferation, which secondary proliferation results in vascular resenosis. This undesirable result can occur after vascular graft surgery, heart transplantation, balloon or laser angioplasty, arterial traumatic injury, postsurgical repair of muscular arteries, long-term in-dwelling of arterial catheters, invasive arterial diagnostic procedures, kidney, lung or liver transplants, coronary artery bypass surgery, carotid artery bypass surgery, femoral popliteal bypass surgery, and intracranial arterial bypass surgery.

In addition to secondary smooth muscle cell proliferation events occurring as a result of trauma, certain diseases are associated with unwanted vascular proliferation, although in these cases, too, it is assumed that some internal unknown injury has caused the secondary result. These disease states include Goodpasture syndrome, acute glomerulonephritis, neonatal pulmonary hypertension, asthma, congestive heart failure, adult pulmonary hypertension, and renal vascular hypertension.

For all these diseases and conditions, administration of suitable amounts of the compositions of the invention is useful in treatment. Administration is by typical routes appropriate for polysaccharide compositions, and generally includes systemic administration, such as by injection. Particularly preferred is intravenous injection, as continuous injection over long time periods can be easily continued. Typical dosage ranges are in the range of 0.1–10 mg/kg/hr on a constant basis over a period of 5–30, preferably 7–14, days. Particularly preferred dosage is about 0.3 mg/kg/hr, or, for a 70 kg adult, 21 mg/hr or 540 mg/day.

Other modes of administration are less preferred but may be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium of formulations is found in *Remington's Pharmaceutical Sciences*, Mack Publishing Company, Easton, Pa., latest edition.

The compositions of the invention may also be labeled using typical methods such as radiolabeling, fluorescent labeling, chromophores or enzymes, and used in a competitive assay for the amount of antiproliferative component in a biological sample. Suitable protocols for competitive assays of analytes in biological samples are well known in the art, and generally involve treatment of the sample, in admixture with the labeled competitor, with a specific binding partner which is reactive with the analyte such as, typically, an immunoglobulin or fragment thereof. The antibodies prepared according to the invention are useful for this purpose. The binding of analyte and competitor to the antibody can be measured by removing the bound complex and assaying either the complex or the supernatant for the label. The separation can be made more facile by preliminary conjugation of the specific binding partner to a solid support. Such techniques are well known in the art, and the protocols available for such competitive assays are too numerous and too well known to be set forth in detail here.

The antibodies of the invention are useful in immunoassays, not only of the type described above involving competition between labeled composition and the analyte antiproliferation factor in the sample, but also for direct immunoassay for the factor. Alternate protocols involving direct assays are also of wide variety and well known. Typically, the analyte bound to antibody is detected by means of an additional reactive partner which bears a label or other means of detection. Thus, in typical sandwich assays, for example, the binding of the antibodies of the invention to analyte can be detected by further reaction with a labeled preparation of these same antibodies or by labeled antibody immunoreactive with this preparation by virtue of species differences.

The antibodies of the invention can also be formulated into pharmaceutical compositions and used to stimulate the growth of smooth muscle cells in subjects for which this result is desirable.

EXAMPLES

The following examples are put forth so as to provide those of ordinary skill in the art with a complete disclosure and description of how to make the compounds and compositions of the invention and are not intended to limit the scope of what the inventors regard as their invention. Efforts have been made to insure accuracy with respect to numbers used (e.g., amounts, temperature, etc.), but some experimental errors and deviations should be accounted for. Unless indicated otherwise, parts are parts by weight, temperature is in degrees centigrade, and pressure is at or near atmospheric.

EXAMPLE 1

Preparation of Hexa- and Octasaccharide Heparin Fragments

To 20 g of heparin dissolved in 160 ml water was added 690 mg solid $NaNO_2$ to give a final HONO concentration of 50 mM in the deamination mixture. Approximately 70 ml 6M HCl was added dropwise while the mixture was stirred with a magnetic stirrer. The pH dropped slowly to 1.5 and was maintained at 1.5 by dropwise addition of either 6M HCl or 2M $Na_2CO_3$. Initially, the addition of acid caused the reaction mixture to turn yellow, but, as the reaction reached completion (about 6 min, when $N_2$ evolution ceased), the solution became clear. When the reaction was complete, 2M $Na_2CO_3$ was added to bring the final pH up to 8.5. A fine white precipitate which sometimes appeared was removed by centrifugation and the supernatant was decanted, degassed under vacuum, and then loaded directly onto a BioGel P10 column.

For the BioGel chromatography, two columns were connected in tandem, each approximately 5 cm in diameter, 128 cm in length, were packed with a total of 5 l. of BioGel P10. The columns were prepared and run in 0.5M $NH_4HCO_3$ at a flow rate of 0.7 ml per min. The deamination mixture was loaded onto the column in the smallest possible volume (less than 160 ml). Fractions of 18 ml were collected and analyzed by the carbazole procedure. Fractions in individual peaks were combined and dried by extensive lyophilization to remove the $NH_4HCO_3$. Peaks containing mixtures of di-, tetra-, hexa-, octa-, deca-, and higher oligosaccharides were obtained, with the higher oligosaccharides eluting early and the disaccharides eluting last.

EXAMPLE 2

Effect on Smooth Muscle proliferation

Solutions to be tested were made up in "complete medium", which is DMEM medium containing 10% fetal calf serum and penicillin/streptomycin.

Bovine smooth muscle cells (SMC) were isolated from bovine pulmonary artery by the method of Ross, R. J., *Cell Biol* (1971) 172–186. SMC from passage 3–10 were plated at 350–700 cells per well in 96-well microtiter plates in the medium above and allowed to attach for 2–4 hr. The complete medium was replaced with DMEM supplemented with 0.1% fetal calf serum, and the cells were incubated for an additional period of about 24 to 72 hr to arrest cell growth. The low-serum medium was then replaced with complete medium containing the test samples.

The cells were allowed to grow for up to 7 days with replicate plates sampled at regular intervals. Cell number was determined by removing the medium and washing the cells with phosphate-buffered saline, adding 75–150 ul lysis buffer, and assaying for lactate dehydrogenase (LDH) activity, as described by Brandley, B., et al., *J Biol Chem* (1987) 262:6431. The activity of LDH is proportional to cell number.

Figure 2:
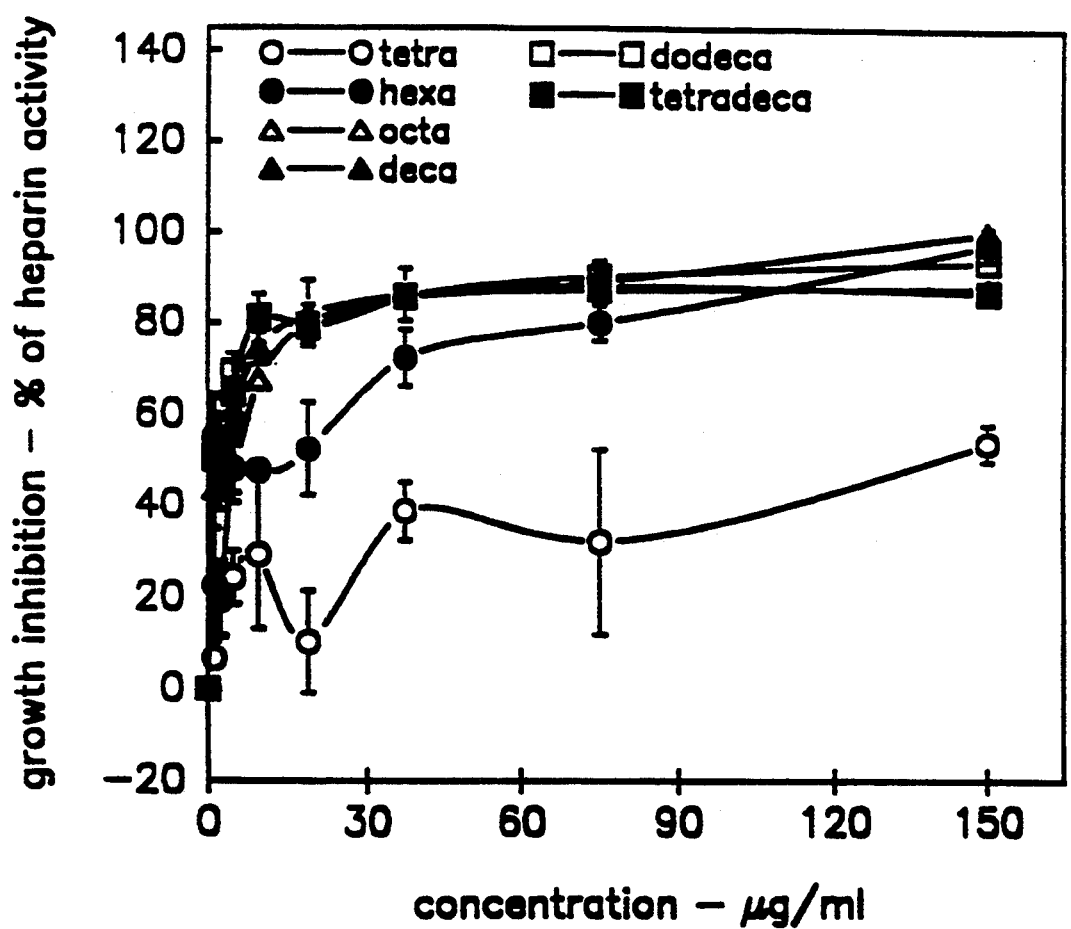
FIG. 2 shows the growth inhibition activity of the various sized fractions.

The results of one such assay on oligosaccharides ranging in size from tetra- to tetradecasaccharide fractions are shown in FIG. 2. These results show that hexasaccharide and octasaccharide fractions are active in the antiproliferative assay; the tetrasaccharide fraction appears substantially less active. While high molecular weight fragments are also active in this assay, fragments of hexasaccharide length and longer have comparable activity to heparin on a concentration weight-/volume basis and shorter oligosaccharides are more conveniently amenable to de novo synthesis. Hence, the minimal unit capable of antiproliferative activity is of interest.

As shown in FIG. 2, 80% inhibition of proliferation is found at concentrations of the octasaccharide fraction as low as 15 ug/ml. Comparable inhibition is shown by the hexasaccharide fraction at about 60 ug/ml.

EXAMPLE 3

Anion Exchange Separation of Hexasaccharides and Octasaccharides

The hexasaccharide and octasaccharide fractions obtained according to Example 1 were subjected to anion exchange chromatography on a 1×7 cm column of DEAE-toyopearl packed in 0.1M $NH_4HCO_3$ and developed with a linear gradient from 0.01M to 1.0M $NH_4HCO_3$ (total volume=600 ml). Approximately 20 mg of each oligosaccharide mixture was loaded onto the column.

Figure 3B:
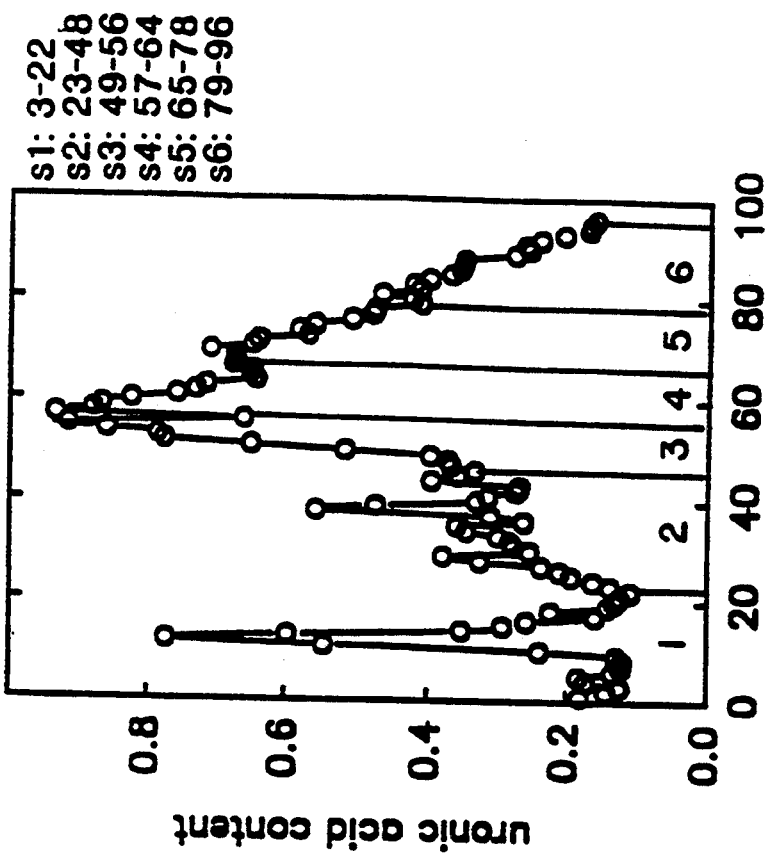
FIGS. 3A and 3B show the elution profiles of hexasaccharide and octasaccharide subunits, respectively, from DEAE-Toyopearl chromatography.
Figure 3A:
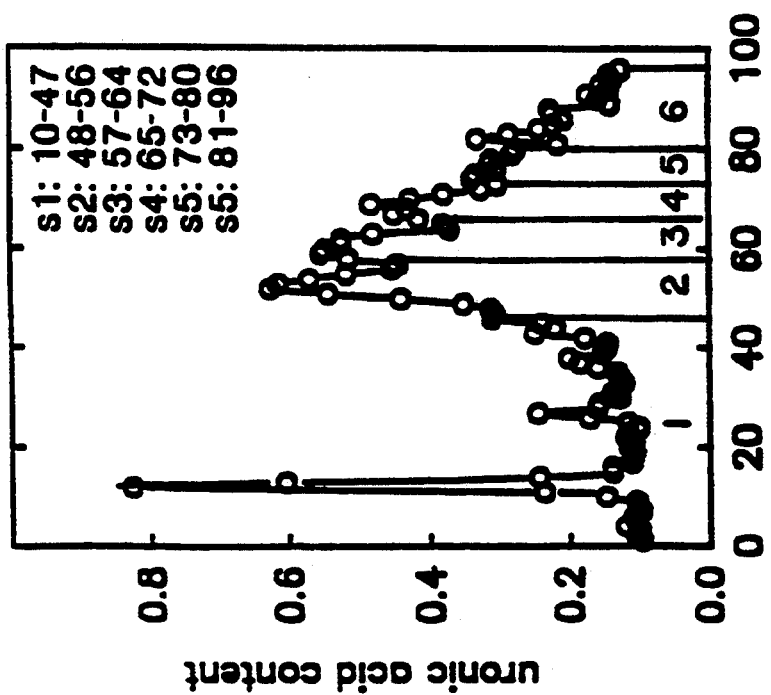

The results are shown in FIG. 3A and 3B for the hexasaccharides and octasaccharides respectively. The eluate was divided into six fractions of equivalent mass as shown in FIGS. 3A and 3B and assayed according to the method of Example 2 for ability to inhibit smooth muscle proliferation. The results of this assay are shown in FIGS. 4A and 4B.

Figure 4A:
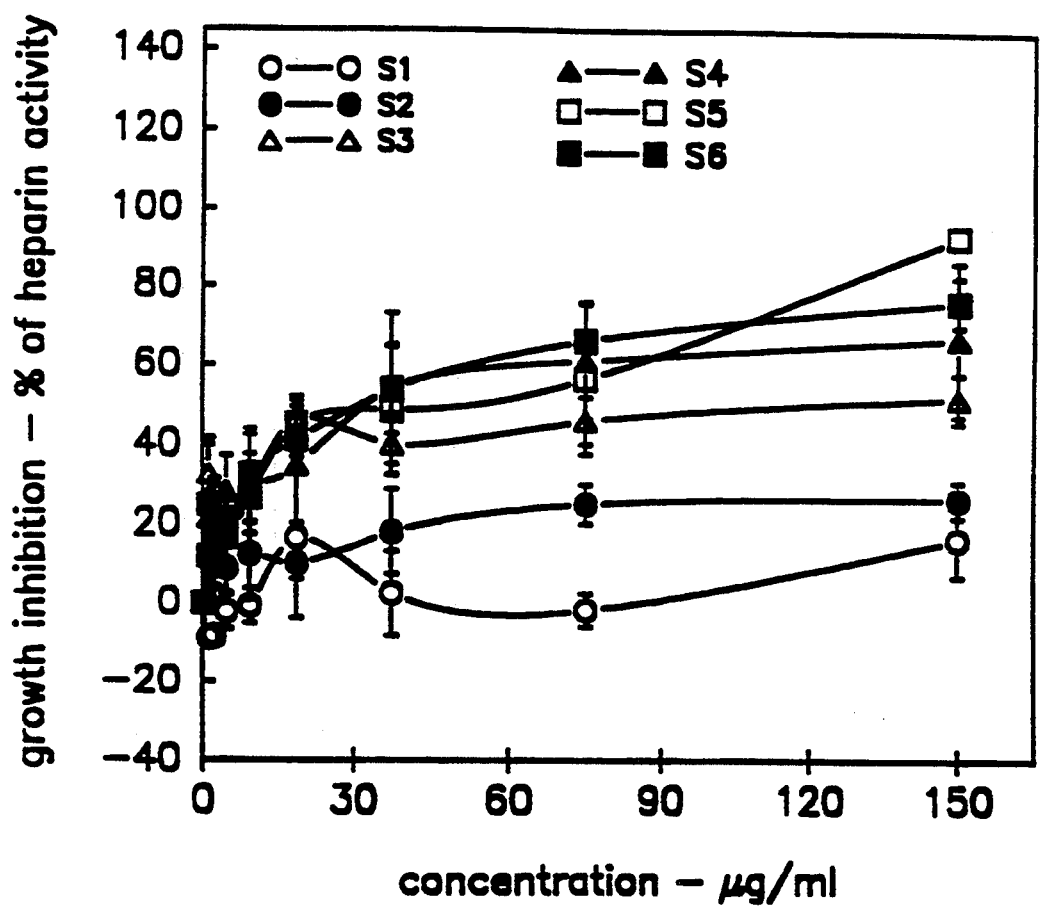
FIGS. 4A and 4B show the growth inhibition activity of various fractions collected in the elution profiles of FIGS. 3A and 3B.
Figure 4B:
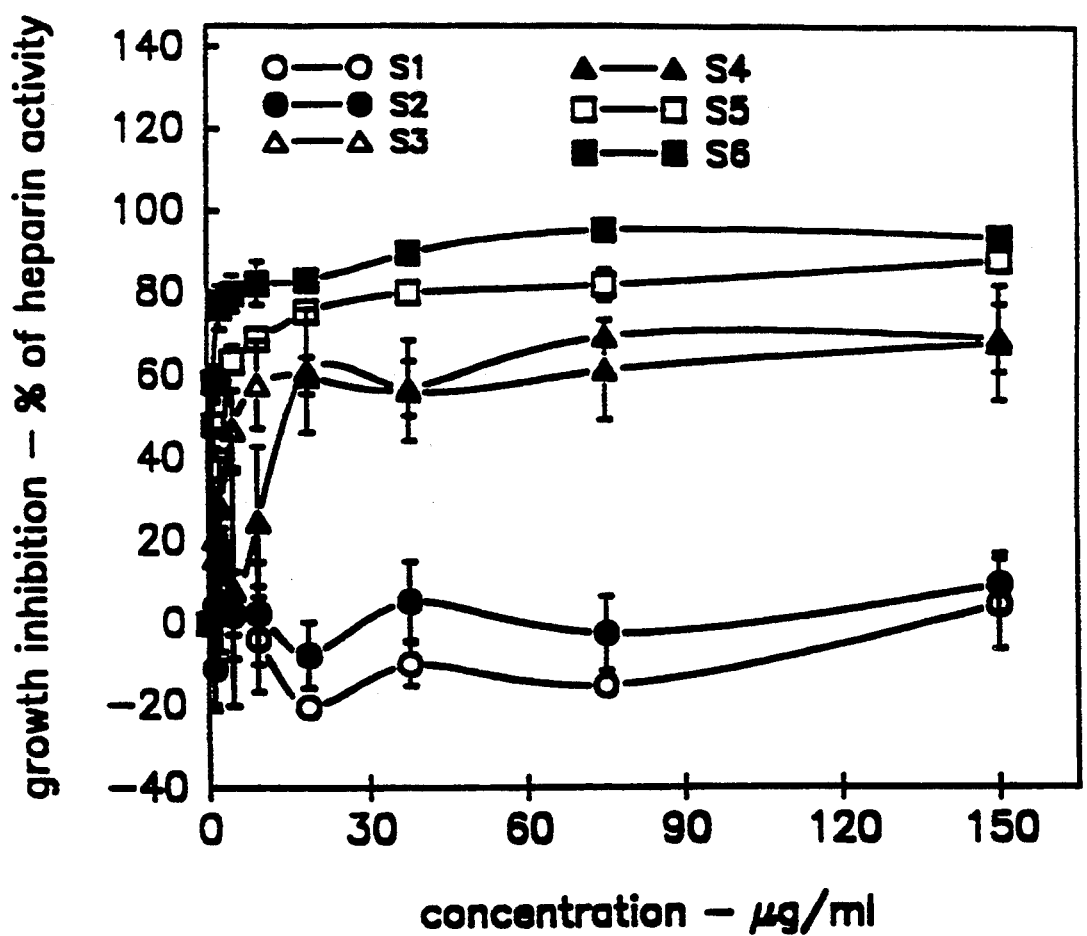

As shown in FIG. 4A, the ability to inhibit smooth muscle proliferation appears correlated with charge, as the highest charged fractions are considerably more effective. Fractions eluting early in either column do not appear to have substantial antiproliferative activity. However, fractions with high affinity for the anion exchanger are quite effective. For example, in the case of the hexasaccharide mixture, concentrations of roughly 75 ug/ml of any of the four highest charged fractions gave inhibition of smooth muscle proliferation in the assay equivalent to 60% of the maximum inhibition obtainable with commercial heparin;the highest charged four fractions of the octasaccharide anion exchange separation were capable of approximately 60–80% inhibition at 15–30 ug/ml.

The DEAE-toyopearl chromatography was run on a larger scale using a 5 cm×27 cm column packed in 0.3M $NH_4HCO_3$. Up to 3 g of oligosaccharide mixture was loaded onto this column and the column was washed successively with 2 l volumes of 0.3M, 0.5M, 0.06M, 0.9M, and 1.2M $NH_4HCO_3$. The fraction emerging in 0.9M $NH_4HCO_3$, equivalent to the most highly sulfated pool from the smaller column, is recovered in yields of approximately 150 mg/g of starting oligosaccharide mixture.

EXAMPLE 4

Reverse Phase Ion Pairing HPLC

The unresolved hexasaccharides and the hexasaccharide fraction which is of the highest charged character obtained from the DEAE-Toyopearl column in Example 3 were subjected to reversed phase ion paring HPLC as described by Guo, Y., et al., *Anal Biochem* (1988) 168:54–62. The elution patterns for these procedures are shown in FIGS. 5A and 5B.

Figure 5A:
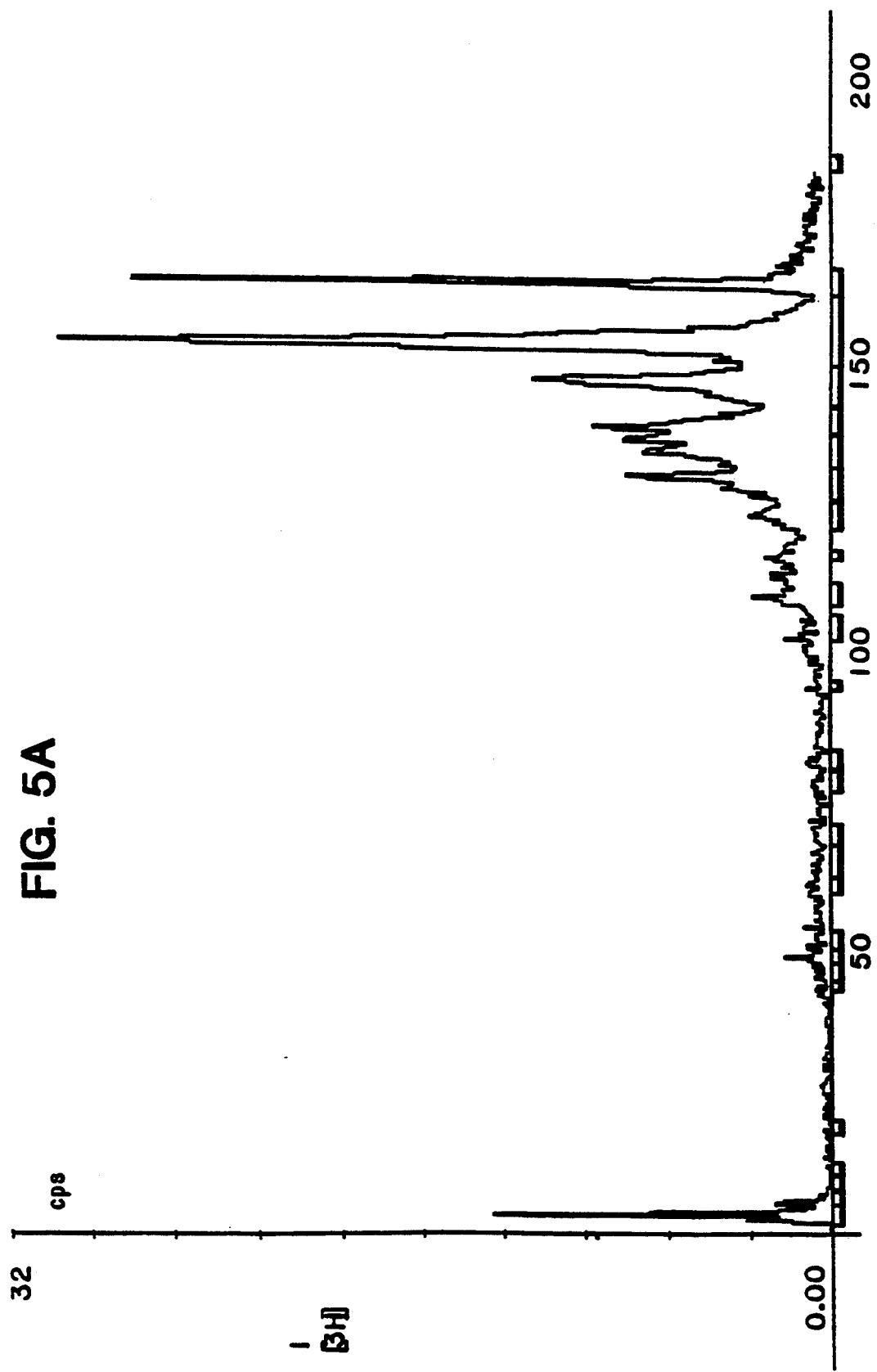
FIG. 5A shows the elution profile from reverse-phase ion-pairing HPLC for the S-6 fraction shown in FIG. 3A.
Figure 5B:
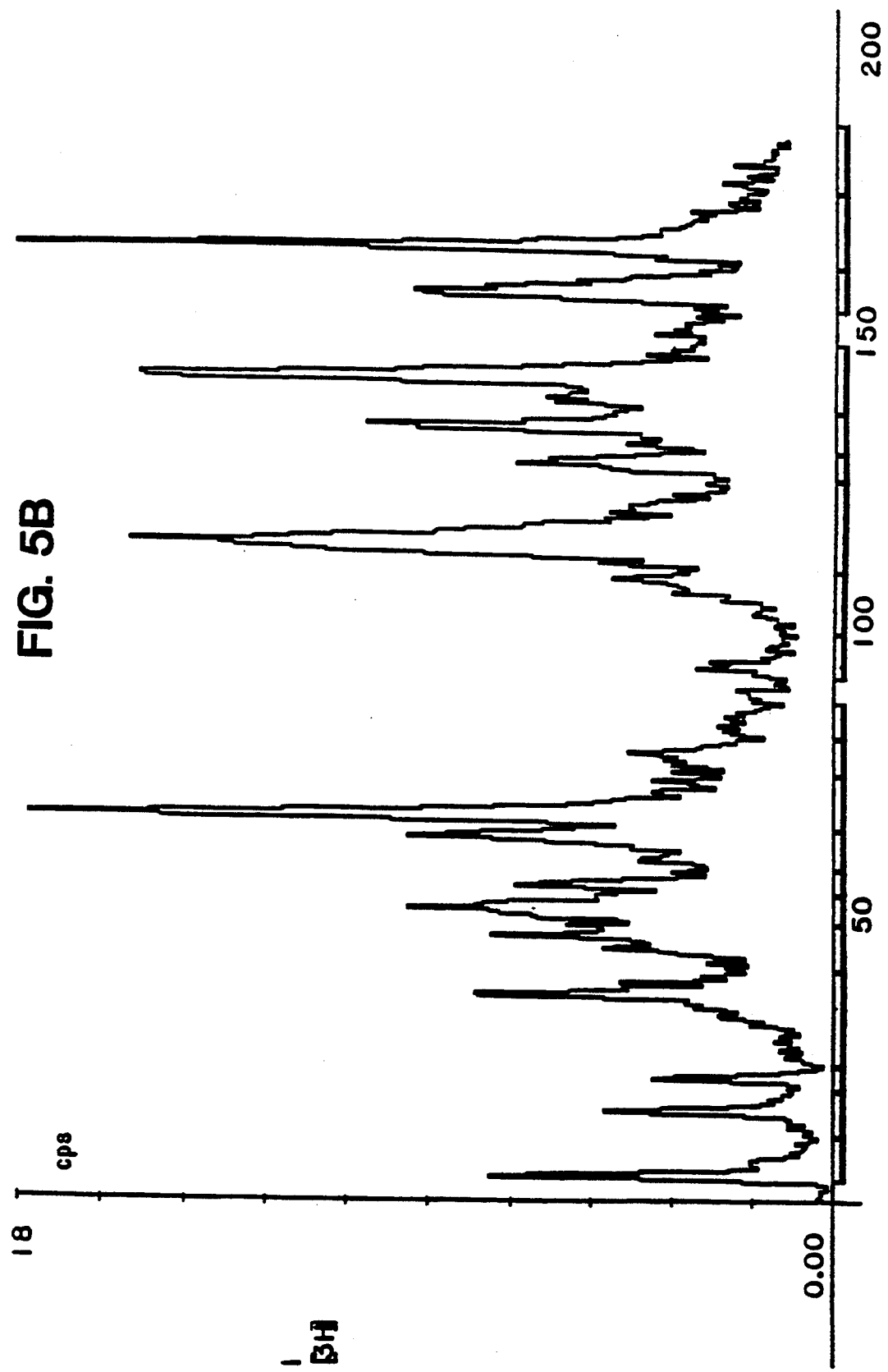
FIG. 5B shows a comparable profile for the total hexasaccharide fraction.

FIG. 5A shows the elution profile from the highest charged fragment of DEAE-Toyopearl; FIG. 5B shows the results using the total hexasaccharide fraction. As a comparison of these profiles will indicate, the charge separated fraction is a greatly simplified mixture. The individual components of this simplified mixture are expected to have antiproliferative activity.

The more highly charged fragments generally show (as compared with less highly charged fragments and/or commercial heparin) (1) a greater ability to inhibit the proliferation of smooth muscle cells and (2) a lesser ability to act as an anticoagulant. Further fractionation/separation processing can be carried out which improve factors (1) and (2) and also simultaneously aid in eliminating fragments which include oligosaccharides sulfated at the 3-position. It is pointed out that in order for a glucosamine to have anticoagulant activity it must be sulfated at the 3-position. Preferred oligosaccharide fragments of the invention possess characteristic (1) and (2) and (3) are highly charged and (4) include a very low (or no) amounts of saccharides sulfated at the 3-position as compared with fragments of commercial heparin. In order to obtain such preferred oligosaccharides, it is preferable to produce them synthetically rather than obtain them from digestion of heparin.

EXAMPLE 5

Synthesis of Preferred Oligosaccharides

As indicated above, the oligosaccharides of the invention which are particularly preferred have a number of distinct characteristics such as greater ability to inhibit proliferation of smooth muscle cells, lesser ability to act an as anticoagulant, high degrees of sulfation, and lack of sulfation at the 3-position. Although it is possible to obtain such particularly preferred oligosaccharides by the digestion of heparin and thereafter separation of the fragments obtained in accordance with methods described above, it is preferable to obtain such particularly preferred fragments using chemical synthesis methodologies. Chemical synthesis methodologies makes it possible to obtain highly pure reaction products all of which have the same structure and therefore characteristics. The following is a flow diagram which shows the synthesis of particularly preferred oligosaccharides. At the end of the structural synthesis schemes put forth below, a written description is provided which describes methods of carrying out such synthesis.

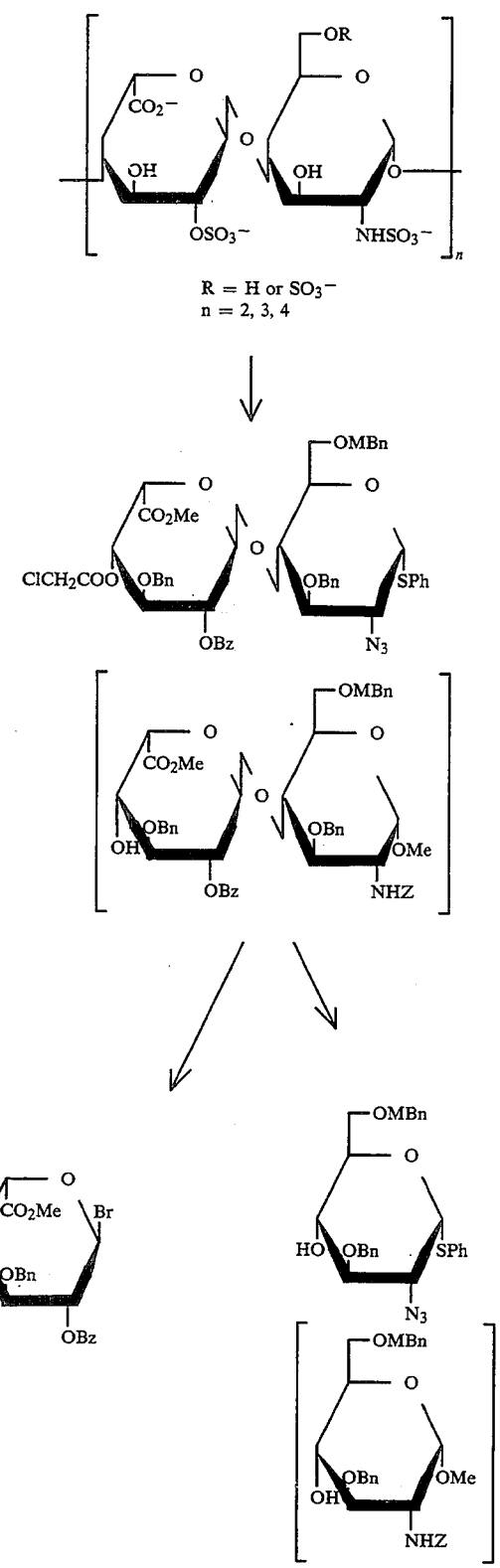

Schematic Structural Retrosynthesis for Making Particularly Preferred Oligosaccharides

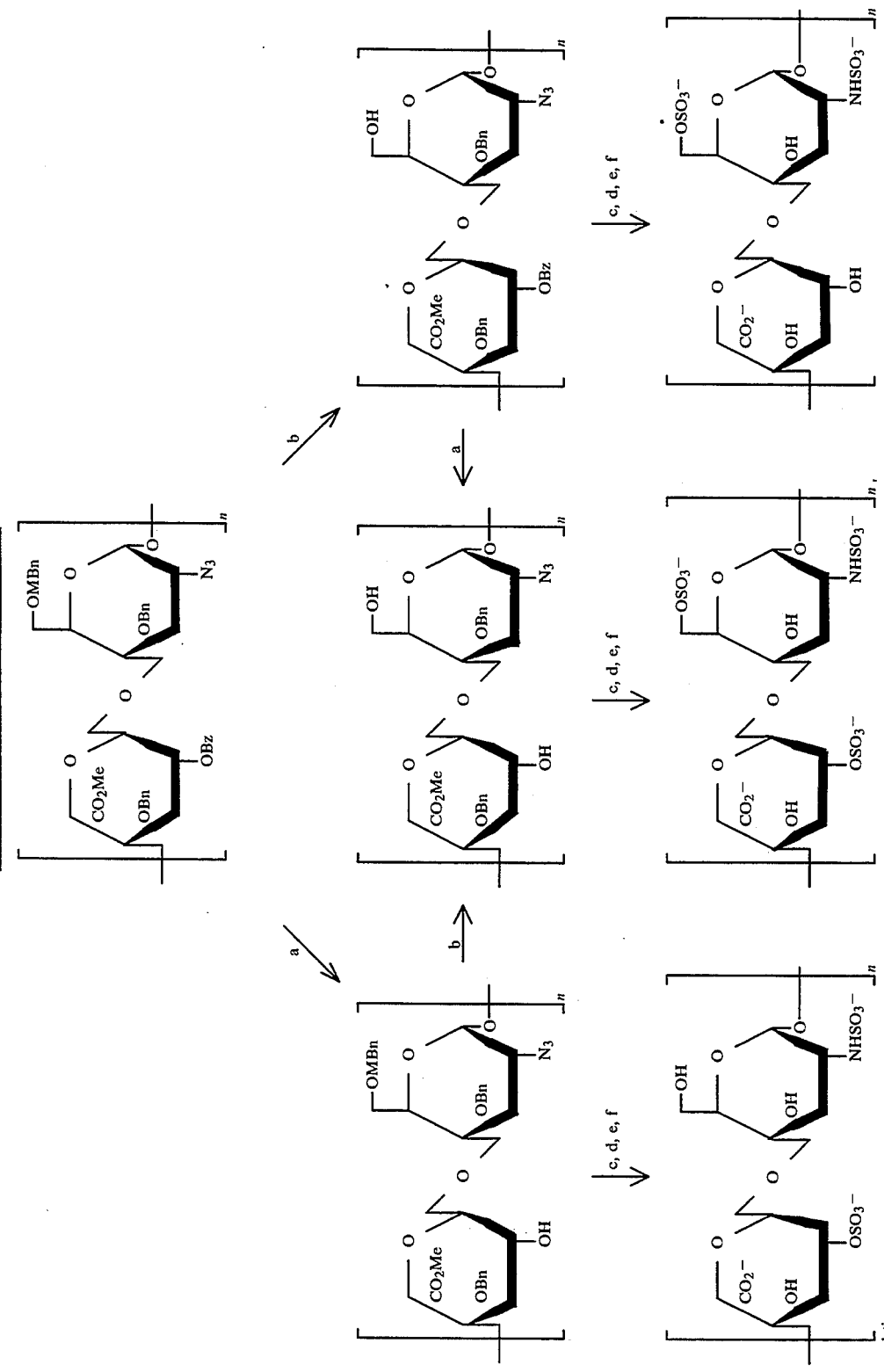

Synthesis of Iduronic Acid Synthon
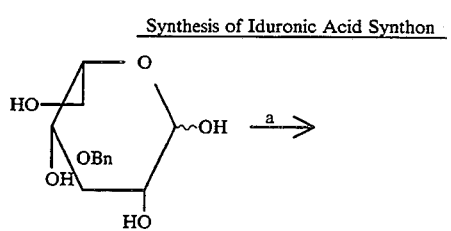
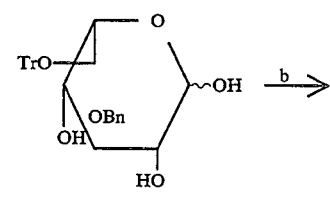
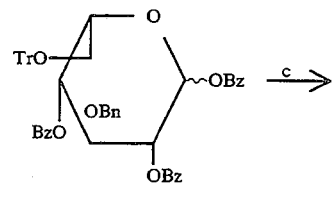
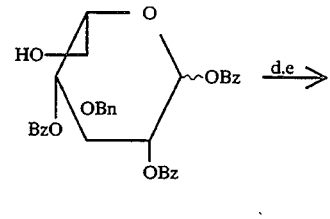
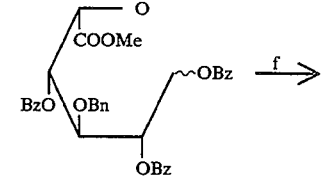
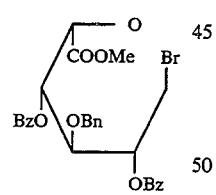
a) TrCl, Pyr;
b) BzCl, Pyr;
c) 80% AcOH;
d) CrO$_3$, acetone;
e) CH$_2$N$_2$, CH$_2$Cl$_2$;
f) TiBr$_4$
Synthesis of Internal Glucosamine Synthon
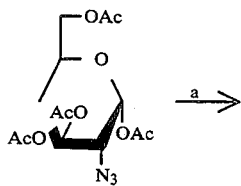
-continued
Synthesis of Internal Glucosamine Synthon
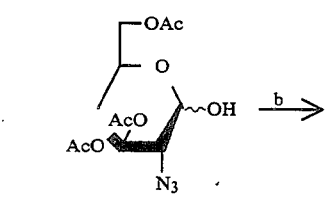
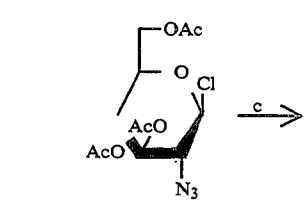
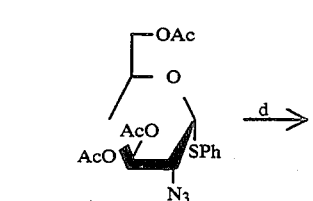
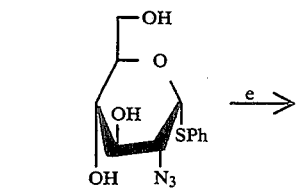
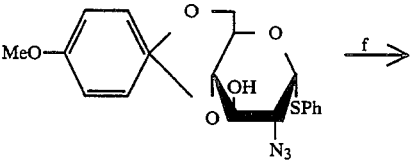
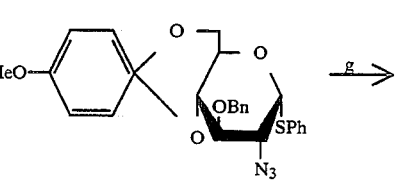
a) hydrazine acetate, DMF;
b) SOCl$_2$, DMF, CH$_2$Cl$_2$;
c) NaSPh, DMF;
d) NaOMe, MeOH;
e) p-methoxybenzaldehyde dimethylacetal, CSA, MeCN;
f) BnBr, NaH, DMF;
g) NaCNBH$_3$, TFA, DMF

Synthesis of Reducing Terminal Glucosamine Synthon
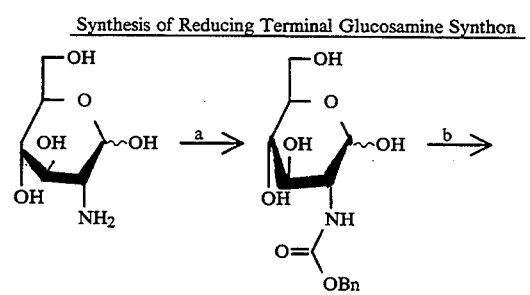
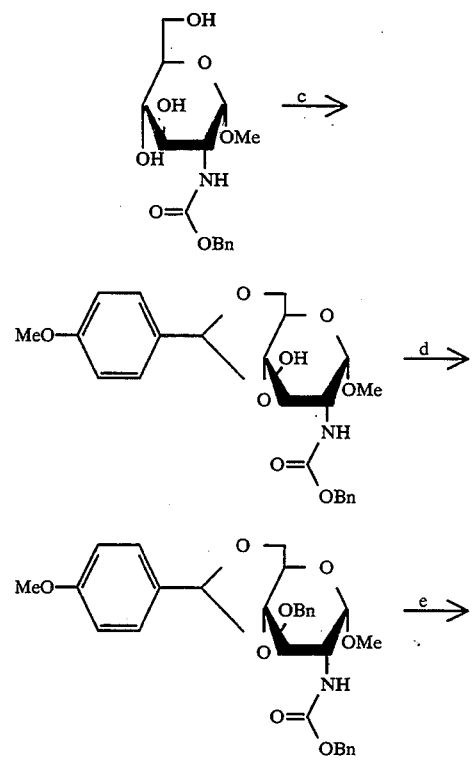
a) ClCOOBn, NaHCO₃, water;
b) MeOH, HCl;
c) p-methoxybenzaldehyde dimethylacetal, CSA, MeCN;
d) BnBr, Ba(OH)₂, DMF;
e) NaCNBH₃, TFA, DMF
Synthesis of Disaccharide Synthons
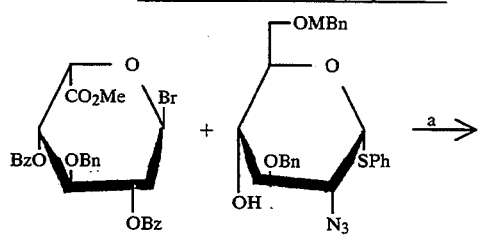
-continued
Synthesis of Disaccharide Synthons
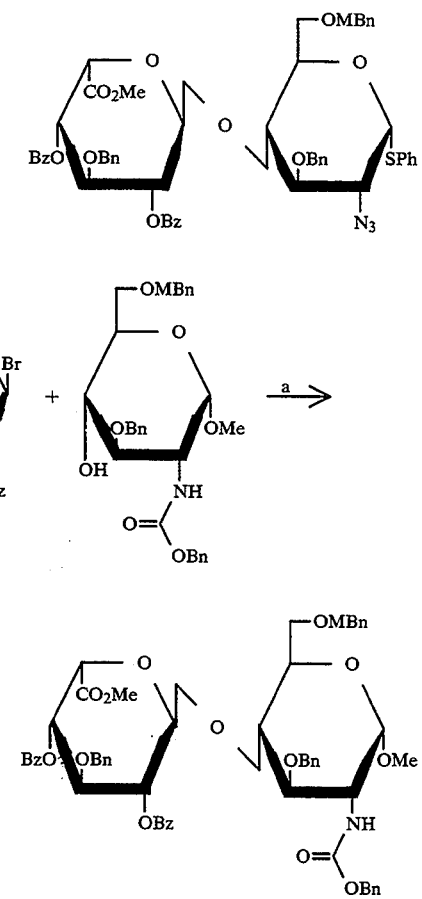
a) AgOTf, collidine, CH₂Cl₂
Functionalization of the Reducing Terminal Disaccharide Synthon
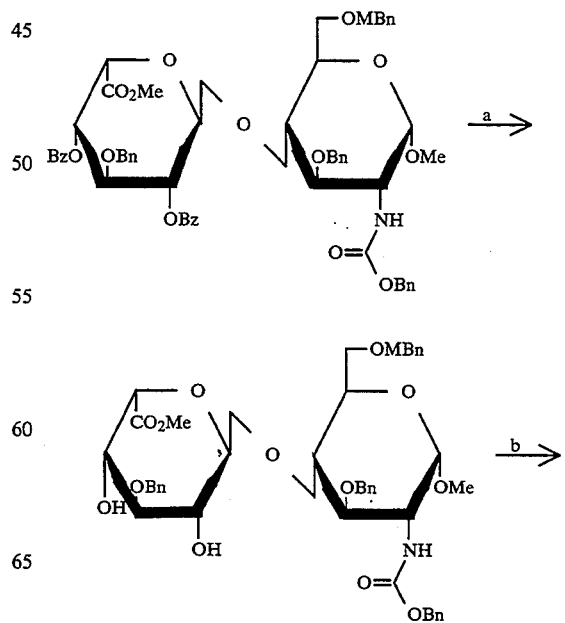

Functionalization of the Reducing Terminal Disaccharide Synthon
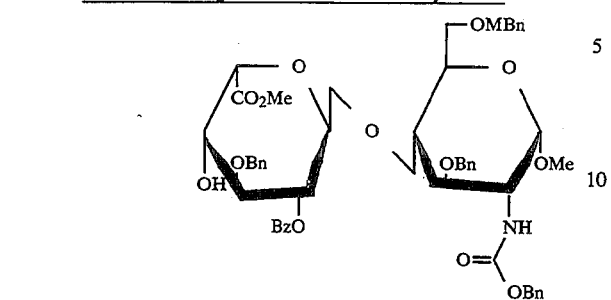
a) NaOMe, MeOH;
b) BzCl, Pyr
Functionalization of the Internal Disaccharide Synthon
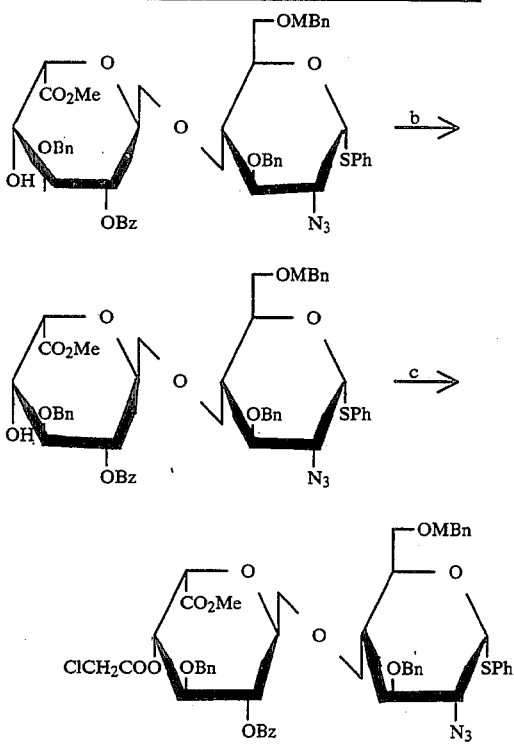
a) NaOMe, MeOH;
b) BzCl, Pyr;
c) chloroacetyl chloride, Pyr, $CH_2Cl_2$
Synthesis of Protected Hexasaccharide
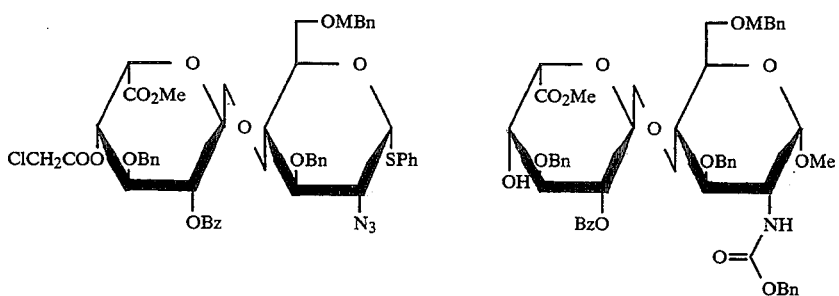
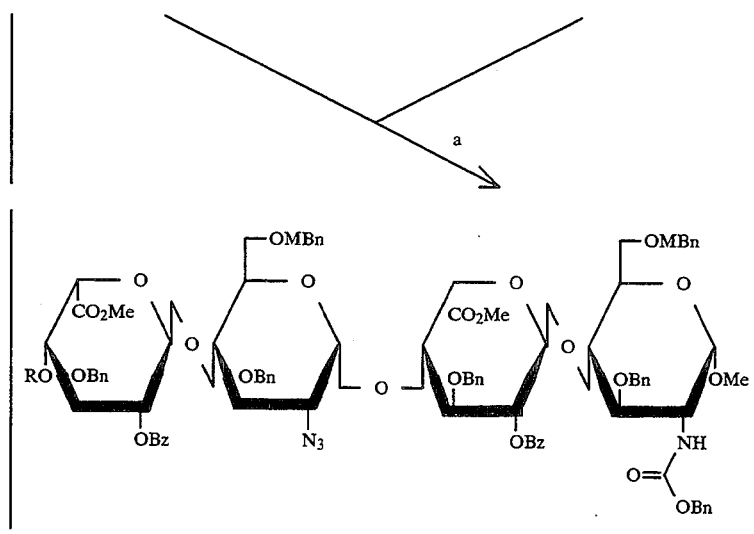

Synthesis of Protected Hexasaccharide -continued

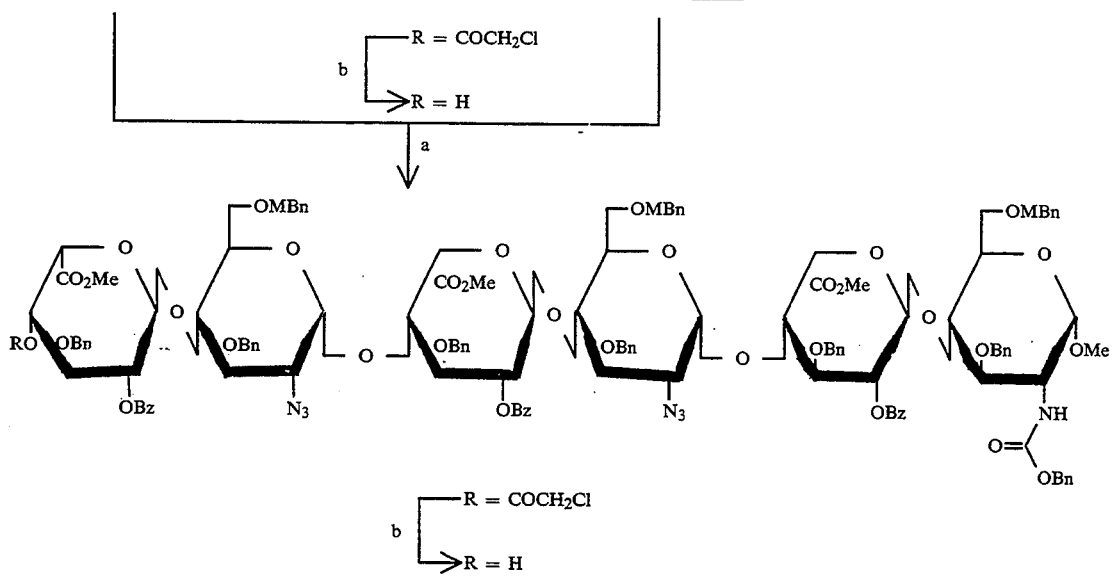

a) DMTST, ether-CH$_2$Cl$_2$;
b) thiourea, EtOAc—MeOH

Retrosynthesis of Particularly Preferred Oligosaccharides

Oligosaccharides, regardless of their size or whether their glucosamine unit is sulfated at 0-6, can be retro-synthesized to a common protected disaccharide unit. This disaccharide unit is open for chain extension in both directions; its thioglycoside function permits chain-extension towards the reducing end, whereas protection of its 0-4' position by the temporary chloracetyl group allows further chain-extensions towards the non-reducing end. The amino groups of the target compounds are masked as azido groups, which assure advantageous stereocontrol in glycosylation reactions. Benzyl (Bn) groups are used as permanent blocking groups for the hydroxyls which are nonsulfated in the target compounds, and the semi-permanent benzoyl (Bz) group is used for the OH's to be sulfated. The p-methoxybenzyl (MBn) group stands for hydroxyl groups the sulfation of which is optional in the target compounds.

The disaccharide synthon should be available by glycosylating the protected 2-azido-2-deoxy-glucopyranosyl derivative with the iduronosyl bromide.

Though all the target oligosaccharides can be synthesized from this single disaccharide synthon, for the particular case of the reducing end this synthon can be substituted by another disaccharide unit (shown in brackets), which bears a methyl glycoside at the reducing end, and an amino group which is protected by a benzyloxycarbonyl (Z) group. This disaccharide can be synthesized by coupling the same iduronic acid donor with a glucosamine derivative shown in brackets.

This retrosynthesis involves a novel and particularly advantageous blocking group strategy, which, in contrast to previous syntheses of sulfated oligosaccharides, permits the preparation of oligosaccharides with different sulfation patterns from the same protected derivative.

The combination of an acyl-type (benzoyl) protecting group with the p-methoxybenzyl group allows specific deprotection and subsequent sulfation in any order, leading to structures which have sulfate groups in positions: a) masked by benzoyl groups in the protected derivative; b) masked by p-methoxybenzyl groups in the protected derivative; and c) masked by both benzoyl and p-methoxybenzyl groups in the protected derivative.

A further advantage of the use of the p-methoxybenzyl group is that if selective removal of this group is not required it can be removed by catalytic hydrogenation in the same step as the permanent benzyl groups, thereby reducing the number of required synthetic steps.

For the synthesis of the iduronic acid donor 3-O-benzyl-L-idose (van Boeckel, C. A. A. et al., Carbohydr Chem (1985) 4:293, incorporated herein by reference) was tritylated with trityl chloride in pyridine and the product, without isolation, was directly benzoylated by the addition of benzoyl chloride to the reaction mixture. The trityl group was removed by acid hydrolysis, and the primary hydroxyl group was oxidized by chromic acid, followed by esterification of the resulting carboxyl group with diazomethane. Conversion to the glycosyl bromide was achieved with titanium(IV) bromide.

For the synthesis of the glucosamine synthon 2-azido-2-deoxy-D-glucose peracetate (Paulsen, H. et al., Chem Ber (1978) 111:2334, incorporated herein by reference) was converted into the thioglycoside in three steps by selective deacetylation with hydrazine acetate (Excoffier, G. et al., Carbohydr Res (1978) 39:368, incorporated herein by reference), followed by conversion of the resulting hemiacetal into the chloride, and subsequent thioglycosidation. The acetyl groups were removed by Zemplen-deacetylation, and the 4,6-O-p-methoxybenzylidene acetal was prepared by an acetal-exchange reaction. The 3-OH group was benzylated, and the 4,6-O-acetal ring was reductively opened with NaCNBH$_3$-trifluoroacetic acid (Johansson, R. et al., J Chem Soc (1984) 1:2371, incorporated herein by reference).

The glucosamine synthon for the reducing end was synthesized by an analogous sequence from methyl 2-benzyloxycarbonylamino-2-deoxy-α-D-glucopyranoside (Heyns, K. et al., *Chem Ber* (1955) 88:188, incorporated herein by reference) by p-methoxybenzylidenation, benzylation, and reductive ring opening.

Coupling of the 2-azido- and 2-benzyloxycarbonylamino-2-deoxy-D-glucose derivatives with the same iduronosyl bromide was performed using silver triflate, in combination with collidine as a buffer of the reaction medium, and resulted in the disaccharides.

Both disaccharides were further functionalized to the disaccharide synthons. The compounds were debenzoylated and a single benzoyl group was introduced at the 0–2' position. In the case of the disaccharide thioglycoside derivative, the benzoylation was followed by chloroacetylation of the 0–4' position.

The two disaccharide synthons were coupled by using dimethyl(methylthio)sulfonium triflate (Fügedi, P. et al., *Carbohydr Res* (1986) 149:C9, incorporated herein by reference) (DMTST) to give the tetrasaccharide with the required α-interglycosidic linkage.

Selective removal of the chloroacetyl group followed by glycosylation with the same disaccharide donor would give the protected hexasaccharide, which can be sulfated and deprotected in different ways as discussed previously.

Additional methods of synthesis may become apparent to those skilled in the art upon reviewing the above disclosure by itself and/or in combination with U.S. Pat. No. 4,943,630 issued Jul. 24, 1990, which patent is incorporated herein by reference to disclose methods of synthesizing oligosaccharides.

While the present invention has been described with reference to specific embodiments thereof, it should be understood by those skilled in the art that various changes may be made and equivalence may be submitted without departing from the true spirit and scope of the invention. In addition, many modifications may be made to adapt a particular situation, material, composition of matter, process, process step or steps, to the objective, spirit and scope of the invention. All such modifications are intended to be within the scope of the claims appended hereto.

We claim:

1. A compound that inhibits the proliferation of smooth muscle cells to a greater extent than commercial heparin, and has a decreased ability to act as an anticoagulant as compared to commercial heparin, the compound having the following structural formula:

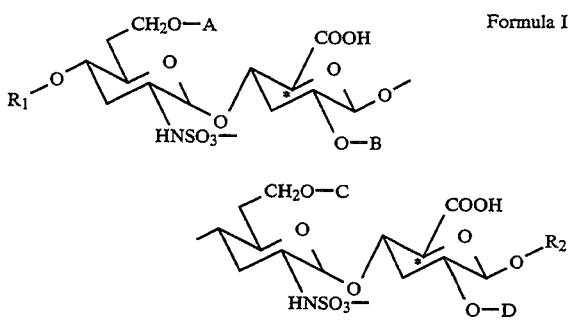

Formula I wherein each of A, B, C, and D is independently H or $SO_3R$ and each R is independently H or a cation, with the proviso that at least two of A, B, C or D is —$SO_3R$; noting that hydroxyl groups on the sugars have been omitted in Formulas I and I(a) for greater clarity and the * adjacent the carbon substituted with COOH indicates any possible stereochemistry in either I or I(a); $R_1$ and $R_2$ are each independently hydrogen or a unit having the following structure:

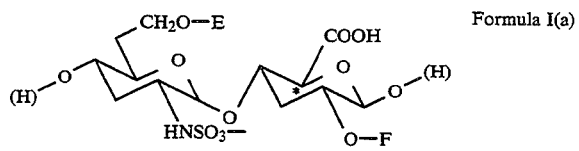

Formula I(a)

wherein when a unit of Formula I(a) is connected at one end, the hydrogen at that end is not present; and each of E and F is independently hydrogen or $SO_3R$ and noting that the hydroxyl group on the 3-position on each sugar is present but has been omitted for greater clarity and further noting that the 3-position is not sulfated.

2. The compound of claim 1, wherein at least three of A, B, C or D are —$SO_3R$.

3. The compound of claim 2, wherein all of A, B, C and D are —$SO_3R$.

4. The compound of claim 1, wherein $R_1$ and $R_2$ are H, and each R is H, ——$Na^+$, $K^+$, $Ca^{2+}$ or $NH_4^+$——.

5. A hexasaccharide and octasaccharide compound that inhibits the proliferation of smooth muscle cells to a greater extent than commercial heparin, and has a decreased ability to act as an anticoagulant as compared to commercial heparin, the compound having the following structural formula:

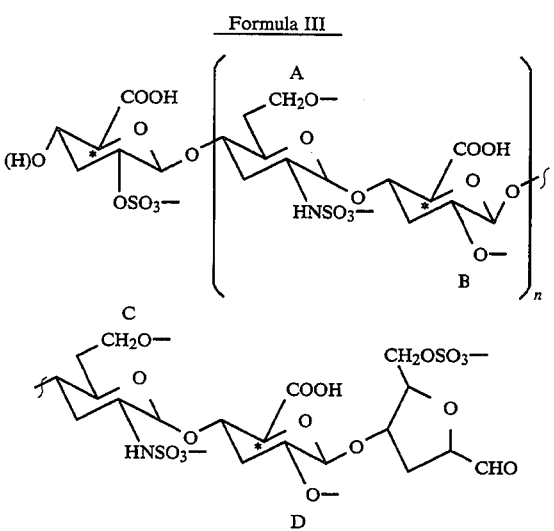

Formula III wherein n is 1 or 2 and each of A, B, C and D is independently H or $SO_3R$, wherein each R is independently H or a cation, with the proviso that at least two of said A, B, C and D are $SO_3R$; and wherein a hydroxyl group present on the 3 position of each sugar is present but has been omitted from the depiction; and noting that the 3-position is not sulfated; and wherein the asterisk on the carbons substituted with carboxyl indicates that the stereochemistry is not determined.

6. A compound of claim 5, wherein at least three of A, B, C or D are —$SO_3R$.

7. A compound of claim 5, wherein at least four of A, B, C or D are —$SO_3R$.

8. A compound of claim 5, wherein at least five of A, B, C or D are —$SO_3R$.

9. A compound of claim 5, wherein all of A, B, C and D are —SO₃R.

10. A compound of claim 5, wherein each R is H, —Na+, K+, Ca²+ or NH₄+——.

11. A hexasaccharide and octasaccharide compound that inhibits the proliferation of smooth muscle cells to a greater extent than commercial heparin, and has a decreased ability to act as an anticoagulant as compared with commercial heparin the compound having the following structural formula:

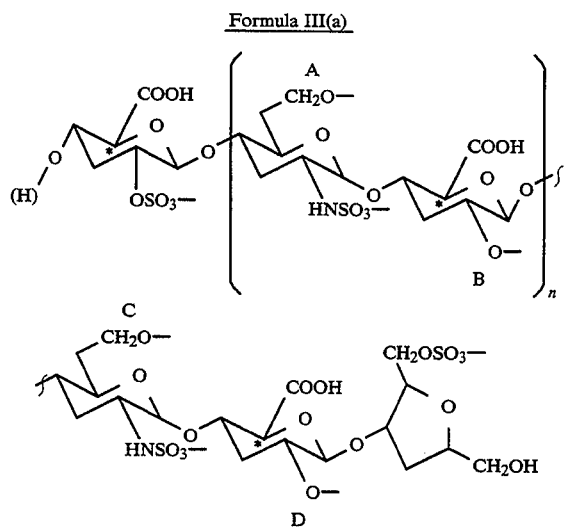

Formula III(a)

wherein n is 1 or 2 and each of A, B, C and D is independently H or SO₃R, wherein each R is independently H or a cation, with the proviso that at least two of said A, B, C and D are SO₃R; and wherein a hydroxyl group present on the 3 position of each sugar is present but has been omitted from the depiction and noting that the 3-position is not sulfated; and wherein the asterisk on the carbons substituted with carboxyl indicates that the stereochemistry is not determined.

12. A compound of claim 11, wherein at least three of A, B, C or D are —SO₃R.

13. A compound of claim 11, wherein at least four of A, B, C or D are —SO₃R.

14. A compound of claim 11, wherein at least five of A, B, C or D are —SO₃R.

15. A compound of claim 11, wherein all of A, B, C and D are —SO₃R.

16. A compound of claim 11, wherein each R is H, —Na+, K+, Ca²+ or NH₄+——.

17. A pharmaceutical composition that inhibits unwanted smooth muscle cell proliferation, comprising:
a pharmaceutically effective amount of a heparin digest derivative in the form of oligosaccharide fragments selected from the group consisting of a hexasaccharide or octasaccharide compound of claim 5 or pharmaceutically acceptable salts thereof which fragments have an increased ability to inhibit smooth muscle cell proliferation and a decreased ability to act as an anticoagulant as compared with commercial heparin; and
a pharmaceutically acceptable carrier.

* * * * *